United States Patent
Abbot et al.

(10) Patent No.: US 10,238,690 B2
(45) Date of Patent: Mar. 26, 2019

(54) MODIFIED T LYMPHOCYTES COMPRISING AN INDUCIBLE CASPASE AND METHODS OF APOPTOSIS

(71) Applicant: CELGENE CORPORATION, Summit, NJ (US)

(72) Inventors: Stewart Abbot, San Diego, CA (US); Tianjian Li, Belle Mead, NJ (US); Bitao Liang, Closter, NJ (US)

(73) Assignee: CELGENE CORPORATION, Summit, NJ (US)

( * ) Notice: Subject to any disclaimer, the term of this patent is extended or adjusted under 35 U.S.C. 154(b) by 0 days.

(21) Appl. No.: 14/775,891

(22) PCT Filed: Mar. 14, 2014

(86) PCT No.: PCT/US2014/027039
§ 371 (c)(1),
(2) Date: Sep. 14, 2015

(87) PCT Pub. No.: WO2014/152177
PCT Pub. Date: Sep. 25, 2014

(65) Prior Publication Data
US 2016/0030479 A1    Feb. 4, 2016

Related U.S. Application Data

(60) Provisional application No. 61/794,294, filed on Mar. 15, 2013.

(51) Int. Cl.
| | |
|---|---|
| *C12N 5/10* | (2006.01) |
| *A61K 38/00* | (2006.01) |
| *A61K 35/17* | (2015.01) |
| *A61K 39/395* | (2006.01) |
| *A61K 38/17* | (2006.01) |
| *C07K 14/705* | (2006.01) |
| *C07K 16/28* | (2006.01) |
| *C12N 5/0783* | (2010.01) |
| *C07K 14/725* | (2006.01) |
| *C12N 9/64* | (2006.01) |
| *A61K 39/00* | (2006.01) |

(52) U.S. Cl.
CPC .......... *A61K 35/17* (2013.01); *A61K 38/1709* (2013.01); *A61K 39/39558* (2013.01); *C07K 14/7051* (2013.01); *C07K 14/70521* (2013.01); *C07K 14/70596* (2013.01); *C07K 16/2803* (2013.01); *C07K 16/2887* (2013.01); *C12N 5/0636* (2013.01); *C12N 9/6475* (2013.01); *A61K 2039/505* (2013.01); *C07K 2317/24* (2013.01); *C07K 2319/03* (2013.01); *C07K 2319/33* (2013.01); *C07K 2319/70* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 7,741,465 B1 | 6/2010 | Eshhar et al. | |
| 8,530,168 B2 * | 9/2013 | Chu | ................. C07K 14/72 |
| 2011/0023137 A1 | 1/2011 | Chu et al. | |
| 2011/0229461 A1 | 9/2011 | Tyson | |
| 2011/0286980 A1 | 11/2011 | Brenner | |
| 2012/0034245 A9 | 2/2012 | Thompson et al. | |
| 2012/0093842 A1 | 4/2012 | Eshhar et al. | |
| 2013/0071414 A1 | 3/2013 | Dotti et al. | |
| 2013/0323834 A1 | 12/2013 | Brenner | |
| 2014/0023647 A1 | 1/2014 | Slawin et al. | |
| 2014/0087468 A1 | 3/2014 | Spencer et al. | |
| 2014/0286987 A1 | 9/2014 | Spencer et al. | |

FOREIGN PATENT DOCUMENTS

| | | |
|---|---|---|
| WO | WO 1996023814 A1 | 8/1996 |
| WO | WO 2011/035018 | 3/2011 |
| WO | WO 2012079000 A1 | 6/2012 |
| WO | WO 2014164348 A2 | 10/2014 |
| WO | WO 2014197638 A2 | 12/2014 |

OTHER PUBLICATIONS

Tsuji et al., Concurrent induction of T-cell activation and apoptosis of osteosarcoma cells by adenovirus-mediated B&-1/Fas chimeric gene transfer, Cancer Gene Ther. 10:717-725, 2003.*
Stasi et al., Inducible apoptosis as a safety switch for adoptive cell therapy, N. Engl. J. Med. 365:1673-1683, 2011.*
Bissonnette et al., Functional Myc-Max heterodimer is required for activation-induced apoptosis in T cell hybridomas, J. Exp. Med 180:2413-2418, Dec. 1994.*
Kametaka et al., Reduction of CTLL-2 cytotoxicity by induction of apoptosis with a Fas-estrogen receptor chimera, Canc. Sci. 94:639-643, 2003.*
Maher, J., Immunotherapy of malignant disease using chimeric antigen receptor engrafted T cells, ISRN Oncology, vol. 2012, Article ID 278093, 23 pages, 2012.*
Straathof et al., 2005, "An inducible caspase 9 safety switch for T-cell therapy," Blood 105(11):4247-4254.
Hoyos et al., 2012, "Genetic modification of human T lymphocytes for the treatment of hematologic malignancies," Haematologica, 97(11):1622-1631.
Introna et al., 2000, "Genetic modification of human T cells with CD20: a strategy to purify and lyse transduced cells with anti-CD20 antibodies," Hum. Gene Ther., 11(4):611-620.

(Continued)

*Primary Examiner* — Claire Kaufman
(74) *Attorney, Agent, or Firm* — Jones Day

(57) ABSTRACT

Provided herein are cells, e.g., T cells expressing artificial cell death polypeptides that cause death of a cell, e.g., cells (e.g., T lymphocytes) expressing the cell death polypeptide, when the cell death polypeptide is multimerized or dimerized. Also provided herein is use of such cells, e.g., T lymphocytes, to treat diseases such as cancer.

12 Claims, No Drawings

Specification includes a Sequence Listing.

(56) References Cited

OTHER PUBLICATIONS

Tey et al., 2007, "Inducible caspase 9 suicide gene to improve the safety of allodepleted T cells after haploidentical stem cell transplantation," Biol. Blood Marrow Transplant., 13(8):913-924.
Thomis et al., 2001, "A Fas-based suicide switch in human T cells for the treatment of graft-versus-host disease," Blood, 97(5):1249-1257.
International Search Report in corresponding PCT Application No. PCT/US2014/027039 dated Jul. 7, 2014 (4 pages).
Written Opinion in corresponding PCT Application No. PCT/US2014/027039 dated Jul. 7, 2014 (14 pages).
Supplemental European Search Report in corresponding European Patent Application No. 14770151.0 dated Aug. 11, 2016 (1 page).

* cited by examiner

US 10,238,690 B2

MODIFIED T LYMPHOCYTES COMPRISING AN INDUCIBLE CASPASE AND METHODS OF APOPTOSIS

This application is a national stage entry of International Patent Application No. PCT/US2014/027039, filed Mar. 14, 2014, which claims priority benefit of U.S. Provisional Patent Application No. 61/794,294, filed Mar. 15, 2013, the disclosure of each of which is incorporated herein by reference in its entirety.

1. FIELD

The disclosure herein relates to the field of immunology, and more specifically, to the modification of T lymphocytes or other immune cells.

2. BACKGROUND

T lymphocytes recognize and interact with specific antigens, including tumor-associated or tumor-specific antigens. Because T lymphocytes are able to kill tumor cells, the last 25 years has seen a great deal of interest in targeting tumor cells with T lymphocytes, either antigen-specific T lymphocytes, or T lymphocytes genetically modified to express one or more chimeric antigen receptors (CARs; see, e.g., Eshhar, U.S. Pat. No. 7,741,465; Eshhar, U.S. Patent Application Publication No. 2012/0093842). However, given the ability of T lymphocytes to kill not only tumor cells displaying a certain antigen but normal cells displaying the same antigen, it is desirable to incorporate into the T lymphocytes a safety mechanism that enables rapid killing of the cells after administration to a patient should off-target effects prove deleterious to the patient.

While a system to kill T cells has described (Straathof et al. (2005) *Blood* 105(11):4247-4254), this system was dependent upon specific and difficult-to-make protein modifications, rendering the system undesirable for practical use. As such, there exists a need in the art for a safety system to rapidly kill therapeutic T lymphocytes that are relatively simple and straightforward to construct. T lymphocytes comprising such a safety system are provided herein.

3. SUMMARY

Provided herein are genetically modified cells, for example immune cells, such as T lymphocytes, e.g., human T lymphocytes, that comprise an artificial multimerizable, e.g., dimerizable, polypeptide (referred to herein as a "cell death polypeptide") that, when multimerized, e.g., dimerized, by a multimerizing agent, e.g., dimerizing agent, generates an apoptosis-inducing signal in a cell, e.g., a T lymphocyte, that expresses the polypeptide, resulting in cell death, e.g., via apoptosis. Without wishing to be bound by any particular mechanism or theory, it is thought that when a sufficient number of a plurality of cell death polypeptides of the cell are multimerized, e.g., dimerized, that the aggregate apoptosis-inducing signal thereby generated is sufficient to kill the cell, e.g., cause the cell to undergo apoptosis.

The cell death polypeptides provided herein may be used in conjunction with any cells, in particular, any mammalian cells, for example, any human cells. For example, such cell death polypeptides provide, for example, a useful safety feature for cell therapeutics. As such, the cell death polypeptides can, for example, be important for a drug product comprising a cell therapeutic, e.g., a chimeric antigen receptor-expressing CAR T lymphocytes, because the cell death polypeptides enable rapid killing of the cell therapeutic, e.g., the T lymphocytes, should such rapid killing become desirable, e.g., in the event administration of the cells causes any unwanted or deleterious effects in a patient receiving them, or if the presence of the cell therapeutic, e.g., the T lymphocytes, in a subject is no longer necessary. Thus, in certain embodiments, the cell death polypeptides provided herein can be used in conjunction with any administrable cells, for example cell therapeutics, such as mammalian cell therapeutics, e.g., human cell therapeutics. Non-limiting examples of cells in which the cell death polypeptides and multimerizing or dimerizing agents may be used include, but are not limited to, natural killer (NK) cells, dendritic cells (DC), placental stem cells (e.g., the placental stem cells disclosed in U.S. Pat. Nos. 7,468,276; 8,057,788 and 8,202,703, the disclosures of which are hereby incorporated by reference in their entireties), mesenchymal-like stem cells from umbilical cord blood, placental blood, peripheral blood, bone marrow, dental pulp, adipose tissue, osteochondral tissue, and the like; embryonic stem cells, embryonic germ cells, neural crest stem cells, neural stem cells, and differentiated cells (e.g., fibroblasts, etc.). The cell death polypeptides, and multimerizing or dimerizing agents, may also be used in tumor cell lines, e.g., for animal model experimental purposes.

Typically, the cell death polypeptide is multimerizable or dimerizable using an administrable multimerizing or dimerizing agent, e.g., a small molecule, polypeptide (other than the cell death polypeptide) such as an antibody, an oligonucleotide, or a polysaccharide. The cell death polypeptides do not comprise a FK506 binding protein (FKBP), functional portion thereof, of modified form thereof, and the multimerizing agent or dimerizing agent is not an FKBP ligand.

In a first aspect, provided herein is a cell, e.g., a T lymphocyte, comprising a cell death polypeptide comprising an apoptosis-inducing domain, wherein said cell death polypeptide is multimerizable using a multimerizing agent, wherein when said multimerizing agent multimerizes said polypeptide, an apoptosis-inducing signal is generated in said cell. In a specific embodiment, said multimerizing agent is a dimerizing agent; that is, the multimerizing agent causes the cell death polypeptide to dimerize. In another specific embodiment, when said dimerizing agent dimerizes said polypeptide, an apoptosis-inducing signal is generated in said cell.

In certain embodiments, said cell death polypeptide is a transmembrane polypeptide comprising an extracellular domain, a transmembrane domain, and an intracellular domain comprising said apoptosis-inducing domain. In particular embodiments, the apoptosis-inducing domain of the cell death polypeptide is or comprises a caspase, e.g., caspase 9, caspase 8, or caspase 3, for example a human caspase 9, caspase 8, or caspase 3.

In certain embodiments, the dimerizing agent is a polypeptide comprising at least two sites that specifically bind to a cell death polypeptide, e.g., an extracellular domain of a cell death polypeptide. In particular embodiments, the polypeptide is an antibody, e.g., an antibody comprising at least two epitope or mimotope binding sites. In certain embodiments, only the antigen binding domain of an antibody is used as a multimerizing or dimerizing agent. In certain embodiments, an extracellular domain of a cell death polypeptide comprises at least one epitope or mimotope to which the antibody specifically binds. In particular embodiments, the antibody is a bispecific antibody comprising two different epitope or mimotope binding sites that bind two different epitopes or mimotopes present on an extracellular domain of a cell death polypeptide. In certain embodiments, the antibody is an IgG or an IgM antibody. In a particular embodiment, an antibody useful as a multimerizing or dimerizing agent is one that has been approved by the United States Food and Drug Administration for any use.

In one embodiment, an antibody useful as a multimerizing or dimerizing agent is one that specifically binds to a CD20 epitope or mimotope, e.g., a human CD20 epitope or mimotope, and an extracellular domain of a cell death polypeptide comprises a CD20 epitope or mimotope to which the antibody specifically binds. In certain specific embodiments, the antibody is rituximab and an extracellular domain of a cell death polypeptide comprises a CD20 epitope or a CD20 mimotope that specifically binds to said rituximab. In another specific embodiment, the antibody is tositumumab and an extracellular domain of a cell death polypeptide comprises a CD20 epitope or a CD20 mimotope that specifically binds to said tositumumab. In yet another embodiment, the antibody is ibritumomab and an extracellular domain of a cell death polypeptide comprises a CD20 epitope or a CD20 mimotope that specifically binds to said ibritumomab. In still another embodiment, the antibody is ofatumumab and an extracellular domain of a cell death polypeptide comprises a CD20 epitope or a CD20 mimotope that specifically binds to said ofatumumab.

In another specific embodiment, the antibody is alemtuzumab and an extracellular domain of a cell death polypeptide comprises a CD52 epitope or a CD52 mimotope that specifically binds to said alemtuzumab. In yet another embodiment, the antibody is basiliximab and an extracellular domain of the cell death polypeptide comprises a CD25 epitope or a CD25 mimotope that specifically binds to said basiliximab. In another embodiment, the antibody is daclizumab and an extracellular domain of a cell death polypeptide comprises a CD25 epitope or a CD25 mimotope that specifically binds to said daclizumab. In still another embodiment, the antibody is brentuximab and an extracellular domain of a cell death polypeptide comprises a CD30 epitope or a CD30 mimotope that specifically binds to said brentuximab. In another embodiment, the antibody is belimumab and an extracellular domain of a cell death polypeptide comprises a B-cell activating factor (BAFF) epitope or a BAFF mimotope that specifically binds to said belimumab. In another embodiment, the antibody is cetuximab and an extracellular domain of a cell death polypeptide comprises an epidermal growth factor receptor (EGFR) epitope or an EGFR mimotope that specifically binds to said cetuximab. In yet another embodiment, the antibody is panitumumab and an extracellular domain of a cell death polypeptide comprises an epidermal growth factor receptor (EGFR) epitope or an EGFR mimotope that specifically binds to said panitumumab. In another embodiment, the antibody is efalizumab and an extracellular domain of a cell death polypeptide comprises an epitope of CD11a or a mimotope of CD11a that specifically binds to said efalizumab. In still another embodiment, the antibody is ipilimumab and an extracellular domain of a cell death polypeptide comprises a CD152 epitope or CD152 mimotope that specifically binds to said ipilimumab. In still another embodiment, the antibody is natalizumab and an extracellular domain of a cell death polypeptide comprises an epitope of alpha-4 integrin or a mimotope of alpha 4 integrin that specifically binds to said natalizumab. In another embodiment, the antibody is basiliximab and an extracellular domain of a cell death polypeptide comprises a CD25 epitope or CD25 mimotope that specifically binds to said basiliximab.

In certain embodiments, when a multimerizing agent or a dimerizing agent binds to at least two cell death polypeptides, dimerization or multimerization of the cell death polypeptides occurs, e.g., dimerization or multimerization of the cell death polypeptides occurs. In certain embodiments, an extracellular domain of a cell death polypeptide is or comprises a receptor or a ligand-binding portion thereof. In a specific embodiment, a multimerizing agent or dimerizing agent is or comprises at least two ligands for said receptor or ligand binding portion thereof. In another specific embodiment, said multimerizing agent or dimerizing agent binds to said receptor or said ligand binding portion thereof on two of the cell death polypeptides, and said polypeptides are multimerized or dimerized, e.g., the intracellular domains of said polypeptides are multimerized or dimerized. In particular embodiments the cell death polypeptides comprise intracellular domains comprising a caspase domain, and multimerization or dimerization of the caspase domains occurs. In specific embodiments, said multimerization or dimerization, for example, multimerization or dimerization of intracellular domains, e.g., multimerization or dimerization of caspase domains, initiates an apoptosis-inducing signal in said cell, e.g., T lymphocyte.

In specific embodiments, when an antibody specifically binds to an epitope or mimotope of at least two cell death polypeptides, dimerization of the cell death polypeptides occurs, e.g., dimerization of the intracellular domains of the cell death polypeptides occurs. In particular embodiments the cell death polypeptides comprise intracellular domains comprising a caspase domain, and dimerization of the caspase domains occurs. In specific embodiments, said dimerization, for example, dimerization of intracellular domains, e.g., dimerization of caspase domains, initiates an apoptosis-inducing signal in said cell, e.g., T lymphocyte.

In certain other embodiments of the cell, e.g., T lymphocyte, said extracellular domain of the cell death polypeptide comprises a ligand for a receptor. In a specific embodiment, said multimerizing agent or dimerizing agent comprises at least two receptors or ligand-binding portions thereof that bind to said ligand. In a specific embodiment, when said multimerizing agent or dimerizing agent binds to said receptor or said ligand binding portion thereof on at least two of the cell death polypeptides, said polypeptides are multimerized or dimerized. In a specific embodiment, when the cell death polypeptides are multimerized or dimerized, an apoptosis-inducing signal is generated in said cell.

In certain other embodiments, an extracellular domain of a cell death polypeptide comprises an artificial oligonucleotide sequence. For example, in particular embodiments, a modified cell, e.g., T lymphocyte, comprises a cell death polypeptide comprising an extracellular domain that comprises an artificial oligonucleotide sequence. In a specific embodiment, a multimerizing or dimerizing agent is or comprises at least one multimerizing or dimerizing oligonucleotide comprising a first oligonucleotide and a second oligonucleotide, optionally joined by a linker, wherein said first oligonucleotide and said second oligonucleotide are complementary to said artificial oligonucleotide sequence. In certain specific embodiments, said first oligonucleotide and said second oligonucleotide have the same sequence. In specific embodiments, said first oligonucleotide and said second oligonucleotide are joined in a head-to-head or tail-to-tail conformation. In specific embodiments, when said multimerizing or dimerizing oligonucleotide of said multimerizing agent or dimerizing agent hybridizes to the artificial oligonucleotide sequence of two of said cell death polypeptides, the cell death polypeptides are multimerized or dimerized. In another specific embodiment, when the cell death polypeptides are multimerized or dimerized, an apoptosis-inducing signal is generated in said cell. In particular embodiments, the cell death polypeptides comprise intracellular caspase domains, and when the intracellular caspase domains are multimerized or dimerized, an apoptosis-inducing signal is generated in said cell.

In certain other embodiments of the cell, e.g., T lymphocyte, said multimerizing or dimerizing agent is an artificial polypeptide comprising two or more binding domains joined by one or more linkers.

In a specific embodiment, provided herein is a cell, e.g., a T lymphocyte, comprising a cell death polypeptide comprising an extracellular domain comprising an epitope, a transmembrane domain, and an intracellular domain comprising a caspase 9, e.g., a human caspase 9, or a functional portion thereof. In another specific embodiment, provided herein is a cell, e.g., a T lymphocyte, comprising an artificial polypeptide comprising an extracellular domain comprising a receptor or ligand-binding portion thereof, and an intracellular domain comprising a caspase 9, e.g., a human caspase 9, or a functional portion thereof. In another specific embodiment, provided herein is a cell, e.g., a T lymphocyte, comprising an artificial polypeptide comprising an extracellular domain comprising a ligand or a receptor-binding portion thereof, wherein said ligand binds a receptor or ligand-binding portion thereof, and an intracellular domain comprising a caspase 9, e.g., a human caspase 9, or functional portion thereof. In a specific embodiment, said cell is a T lymphocyte.

In another aspect, provided herein is cell, e.g., a T lymphocyte, safety system comprising a cell comprising (a) a cell death polypeptide comprising an extracellular domain comprising an epitope, a transmembrane domain, and an intracellular domain comprising a caspase or a functional portion thereof; and (b) a dimerizing agent comprising two epitope-binding or mimotope-binding domains that when contacted with two of said cell death polypeptides dimerizes said polypeptides, wherein said caspase is caspase 3, caspase 8 or caspase 9, e.g., human caspase 3, caspase 8, or caspase 9, and wherein said dimerization generates an apoptosis-inducing signal in said cell. In a specific embodiment, said cell is a T lymphocyte.

In another embodiment, provided herein is a cell, e.g., a T lymphocyte, safety system comprising (a) a cell comprising an artificial polypeptide comprising an extracellular domain comprising a receptor or ligand-binding portion thereof, and an intracellular domain comprising a caspase or a functional portion thereof; and (b) a dimerizing agent comprising two ligands that bind to said receptor or ligand-binding portion thereof, wherein when said dimerizing agent is contacted with two of said polypeptides said dimerizing agent dimerizes said polypeptides, wherein said caspase is caspase 3, caspase 8 or caspase 9, e.g., human caspase 3, caspase 8, or caspase 9, and wherein said dimerization generates an apoptosis-inducing signal in said cell. In a specific embodiment, said cell is a T lymphocyte.

In another embodiment, provided herein is a cell, e.g., a T lymphocyte, safety system comprising (a) a cell comprising an artificial cell death polypeptide comprising an extracellular domain comprising a ligand or a receptor-binding portion thereof, and an intracellular domain comprising a caspase or functional portion thereof; and (b) a dimerizing agent comprising two receptors or ligand-binding portions thereof that bind to said ligand or receptor-binding portion thereof, wherein when said dimerizing agent is contacted with two of said polypeptides said dimerizing agent dimerizes said polypeptides, wherein said caspase is caspase 3, caspase 8 or caspase 9, e.g., human caspase 3, caspase 8, or caspase 9, and wherein said dimerization generates an apoptosis-inducing signal in said cell. In a specific embodiment, said cell is a T lymphocyte.

In a specific embodiment of any of the embodiments herein, when a plurality of said apoptosis-inducing signals are generated in said cell, e.g., T lymphocyte, said signal is sufficient to kill said cell. In a specific embodiment, said cell is a T lymphocyte.

In another aspect, further provided herein is a method of killing a cell, e.g., a T lymphocyte, wherein said cell comprises a plurality of artificial cell death polypeptides each comprising an apoptosis-inducing domain, wherein the cell death polypeptides are multimerizable or dimerizable using a multimerizing agent or dimerizing agent that is not an FK506 binding protein (FKBP) ligand, and wherein when said multimerizing agent or dimerizing agent multimerizes or dimerizes said polypeptide, an apoptosis-inducing signal is generated in said T lymphocyte, comprising contacting said cell with an amount of said multimerizing agent or dimerizing agent sufficient for said plurality of the cell death polypeptides to multimerize or dimerize and generate an aggregate apoptosis-inducing signal sufficient to kill said cell. In certain embodiments, the cell death polypeptide is a transmembrane polypeptide comprising an extracellular domain, a transmembrane domain, and an intracellular domain comprising said apoptosis-inducing domain. In specific embodiments, said apoptosis-inducing domain of said polypeptide is or comprises a caspase, e.g., caspase 3, caspase 8 or caspase 9, for example a human caspase 9, caspase 8, or caspase 3. In specific embodiments, the multimerizing agent or dimerizing agent is a protein, an oligonucleotide or a polysaccharide. In a specific embodiment, said cell is a T lymphocyte.

In certain embodiments, the multimerizing agent or dimerizing agent is a protein, an oligonucleotide, or a polysaccharide. In specific embodiments, the multimerizing agent or dimerizing agent is a polypeptide comprising at least two sites that specifically bind to a cell death polypeptide, e.g., an extracellular domain of a cell death polypeptide. In particular embodiments, the polypeptide is an antibody, e.g., an antibody that comprises at least two epitope-binding sites or at least two mimotope-binding sites. In certain embodiments, an extracellular domain of a cell death polypeptide comprises at least one epitope or mimotope to which the antibody specifically binds. In particular embodiments, the antibody is a bispecific antibody comprising two different epitope or mimotope binding sites that bind two different epitopes or mimotopes present on an extracellular domain of a cell death polypeptide. In certain embodiments, the antibody is an IgG or an IgM antibody. In a specific embodiment, an antibody useful as a multimerizing or dimerizing agent is one that has been approved by the United States Food and Drug Administration for any use.

In a specific embodiment, when the multimerizing agent or dimerizing agent is an antibody, said antibody is one that specifically binds to a CD20 epitope or mimotope, e.g., a human CD20 epitope or mimotope, and said extracellular domain of a cell death polypeptide comprises a CD20 epitope or mimotope to which said antibody specifically binds. In certain specific embodiments, when the multimerizing agent or dimerizing agent is an antibody, said antibody is rituximab and said extracellular domain of the cell death polypeptide comprises a CD20 epitope or a CD20 mimotope that binds to said rituximab; said antibody is tositumumab and said extracellular domain of the cell death polypeptide comprises a CD20 epitope or a CD20 mimotope that binds to said tositumumab; said antibody is ibritumomab and said extracellular domain of the cell death polypeptide comprises a CD20 epitope or a CD20 mimotope that binds said ibritumomab; said antibody is ofatumumab and said extracellular domain of the cell death polypeptide comprises a CD20 epitope or a CD20 mimotope that binds said ofatumumab; said antibody is alemtuzumab and said extracellular domain of the cell death polypeptide comprises a CD52 epitope or a CD52 mimotope that binds to said alemtuzumab; said antibody is basiliximab and said extracellular domain of the cell death polypeptide comprises a CD25 epitope or a CD25 mimotope that binds said basiliximab; said antibody is daclizumab and said extracellular domain of the cell death polypeptide comprises a CD25 epitope or a CD25 mimotope that binds said daclizumab; said antibody is brentuximab and said extracellular domain of the cell death polypeptide comprises a CD30 epitope or a CD30 mimotope that binds said brentuximab; said antibody is belimumab and said extracellular domain of the cell death polypeptide comprises a B-cell activating factor (BAFF) epitope or a BAFF mimotope that binds said belimumab; said antibody is cetuximab and said extracellular domain of the cell death polypeptide comprises an epidermal growth factor receptor (EGFR) epitope or an EGFR mimotope that binds said cetuximab; said antibody is panitumumab and said extracellular domain of the cell death polypeptide comprises an epidermal growth factor receptor (EGFR) epitope or an EGFR mimotope that binds said panitumumab; said antibody is efalizumab and said extracellular domain of the cell death polypeptide comprises an epitope of CD11a or a mimotope of CD11a that binds to said efalizumab; said antibody is ipilimumab and said extracellular domain of the cell death polypeptide comprises a CD152 epitope or CD152 mimotope that binds said ipilimumab; said antibody is natalizumab and said extracellular domain of the cell death polypeptide comprises an epitope of alpha-4 integrin or a mimotope of alpha 4 integrin that binds said natalizumab; or said antibody is basiliximab and said extracellular domain of the cell death polypeptide comprises a CD25 epitope or CD25 mimotope that binds said basiliximab. In a specific embodiment of any of the above embodiments, when said antibody binds to said epitope or mimotope on at least two of said cell death polypeptides, the intracellular domains of said polypeptides, and/or the respective caspases in said intracellular domains multimerize or dimerize. In specific embodiments, when said antibody specifically binds to an epitope or mimotope of at least two cell death polypeptides, dimerization of the cell death polypeptides occurs, e.g., dimerization of the intracellular domains of the cell death polypeptides occurs. In particular embodiments the cell death polypeptides comprise intracellular domains comprising a caspase domain, and dimerization of the caspase domains occurs. In specific embodiments, said dimerization, for example, dimerization of intracellular domains, e.g., dimerization of caspase domains, initiates an apoptosis-inducing signal in said cell, e.g., T lymphocyte.

In certain specific embodiments, said extracellular domain of the cell death polypeptide is or comprises a receptor or a ligand-binding portion thereof. In such embodiments, said multimerizing agent or dimerizing agent comprises at least two ligands for said receptor or ligand binding portion thereof. In specific embodiments, when said multimerizing agent or dimerizing agent binds to said receptor or said ligand binding portion thereof on at least two of said cell death polypeptides, said polypeptides are multimerized or dimerized. In specific embodiments, said multimerization or dimerization of said polypeptides initiates an apoptosis-inducing signal in said cell, e.g., T lymphocyte.

In certain specific embodiments, said extracellular domain of the cell death polypeptide comprises a ligand for a receptor. In such embodiments, said multimerizing agent or dimerizing agent comprises at least two receptors or ligand-binding portions thereof that bind to said ligand. In specific embodiments, when said multimerizing agent or dimerizing agent binds to said receptor or said ligand binding portion thereof on two or more of said polypeptides, the intracellular domains in said polypeptides and/or the caspase domains of said polypeptides are multimerized or dimerized. In specific embodiments, said multimerization or dimerization of said intracellular domains and/or caspase domains initiates an apoptosis-inducing signal is generated in said cell, e.g., T lymphocyte.

In certain embodiments, said extracellular domain of said cell death polypeptide comprises an artificial oligonucleotide sequence. For example, in particular embodiments, said cell death polypeptide comprises an extracellular domain that comprises an artificial oligonucleotide sequence. In a specific embodiment, a multimerizing or dimerizing agent is or comprises at least one multimerizing or dimerizing oligonucleotide comprising a first oligonucleotide and a second oligonucleotide, optionally joined by a linker, wherein said first oligonucleotide and said second oligonucleotide are complementary to said artificial oligonucleotide sequence. In certain specific embodiments, said first oligonucleotide and said second oligonucleotide have the same sequence. In specific embodiments, said first oligonucleotide and said second oligonucleotide are joined in a head-to-head or tail-to-tail conformation. In specific embodiments, when said multimerizing or dimerizing oligonucleotide of said multimerizing agent or dimerizing agent hybridizes to the artificial oligonucleotide sequence of two of said cell death polypeptides, the cell death polypeptides are multimerized or dimerized. In another specific embodiment, when the cell death polypeptides are multimerized or dimerized, an apoptosis-inducing signal is generated in said cell. In particular embodiments, the cell death polypeptides comprise intracellular caspase domains, and when the intracellular caspase domains are multimerized or dimerized, an apoptosis-inducing signal is generated in said cell. In a specific embodiment, said cell is a T lymphocyte.

In a specific embodiment of any of the embodiments herein, when a plurality of said apoptosis-inducing signals are generated in said T lymphocyte, said signal is sufficient to kill said cell, e.g., T lymphocyte.

In other embodiments, said multimerizing agent or dimerizing agent is an artificial polypeptide comprising two or more binding domains joined by one or more linkers.

In a specific embodiment, provided herein is a method of killing a cell, e.g., a T lymphocyte, wherein said cell comprises a plurality of artificial cell death polypeptides each comprising a caspase or functional portion thereof, wherein said caspase is caspase 3, caspase 8 or caspase 9 (e.g., human caspase 3, caspase 8, or caspase 9), and, wherein said cell death polypeptide is dimerizable using an antibody, and wherein when said antibody dimerizes said polypeptide, an apoptosis-inducing signal is generated in said cell, comprising contacting said cell with an amount of said antibody sufficient to dimerize a sufficient number of said plurality of artificial polypeptides to dimerize and generate an aggregate apoptosis-inducing signal sufficient to kill said cell. In a specific embodiment, said cell is a T lymphocyte.

In another specific embodiment, provided herein is a method of killing a cell, e.g., a T lymphocyte, wherein said cell comprises a plurality of artificial cell death polypeptides each comprising a caspase or functional portion thereof, wherein said caspase is caspase 3, caspase 8 or caspase 9 (e.g., human caspase 3, caspase 8, or caspase 9), and, wherein said plurality of artificial polypeptides each comprises an extracellular domain comprising a receptor or ligand-binding portion thereof that bind a ligand, wherein said polypeptide is dimerizable using a dimerizing agent comprising two said ligands, and wherein when said dimerizing agent dimerizes two of said polypeptides, an apoptosis-inducing signal is generated in cell, comprising contacting said cell with an amount of said dimerizing agent sufficient to dimerize a sufficient number of said plurality of artificial cell death polypeptides to dimerize and generate an aggregate apoptosis-inducing signal sufficient to kill said cell. In a specific embodiment, said cell is a T lymphocyte.

In another specific embodiment, provided herein is a method of killing a cell, e.g., a T lymphocyte, wherein said cell comprises a plurality of artificial cell death polypeptides each comprising a caspase or functional portion thereof, wherein said caspase is caspase 3, caspase 8 or caspase 9 (e.g., human caspase 3, caspase 8, or caspase 9), and, wherein said plurality of artificial polypeptides each comprises an extracellular domain comprising a ligand or receptor-binding portion thereof that bind a receptor or ligand-binding portion thereof, wherein said polypeptides are dimerizable using a dimerizing agent comprising two said receptors or ligand-binding portion thereof, and wherein when said dimerizing agent dimerizes two of said polypeptides, an apoptosis-inducing signal is generated in said cell, comprising contacting said cell with an amount of said dimerizing agent sufficient to dimerize a sufficient number of said plurality of artificial polypeptides to dimerize and generate an aggregate apoptosis-inducing signal sufficient to kill said cell. In a specific embodiment, said cell is a T lymphocyte.

In another specific embodiment, provided herein is a method of killing a cell, e.g., a T lymphocyte, wherein said cell comprises a plurality of artificial cell death polypeptides each comprising a caspase or functional portion thereof, wherein said caspase is caspase 3, caspase 8 or caspase 9 (e.g., human caspase 3, caspase 8, or caspase 9), and, wherein said plurality of artificial polypeptides each comprising an extracellular domain comprising an artificial oligonucleotide, wherein said plurality of polypeptides are dimerizable using a dimerizing agent comprising an oligonucleotide comprising a first oligonucleotide and a second oligonucleotide, wherein said first oligonucleotide and said second oligonucleotide have the same nucleotide sequence, and wherein said first oligonucleotide and second oligonucleotide optionally are joined by a linker, and wherein said first oligonucleotide and said second oligonucleotide are complementary to said artificial oligonucleotide in said extracellular domain of said polypeptide, and wherein when said dimerizing agent dimerizes two of said cell death polypeptides, an apoptosis-inducing signal is generated in said cell, comprising contacting said cell with an amount of said dimerizing agent sufficient to dimerize a sufficient number of said plurality of artificial polypeptides to dimerize and generate an aggregate apoptosis-inducing signal sufficient to kill said cell. In a specific embodiment, said cell is a T lymphocyte.

In certain embodiments, the cells (e.g., T lymphocytes) killed in accordance with the methods described herein comprise a polypeptide that acts to target the cell to a particular antigen, e.g., a tumor-associated antigen or tumor-specific antigen, wherein said polypeptide, when bound to said antigen, causes the cell to kill a cell displaying said antigen, for example, a chimeric antigen receptor (CAR). T lymphocytes comprising CARs are referred to herein as CAR-T lymphocytes. The chimeric antigen receptors typically comprise (i) an intracellular domain (e.g., cytoplasmic domain) of an endogenous protein expressed on the surface of lymphocytes and that triggers the activation and/or proliferation of said lymphocytes, (ii) a transmembrane domain, and (iii) an extracellular domain that binds to an antigen of interest, e.g., a tumor-associated antigen or tumor-specific antigen. The CAR-T lymphocytes also typically comprise one or more co-stimulatory domains. In certain embodiments, a CAR-T lymphocyte comprises at least two CAR polypeptides, at least one of which provides a primary stimulatory signal to the CAR-T lymphocyte, and at least one that provides a costimulatory signal to the CAR-T lymphocyte. CAR-T lymphocytes comprising a cell death polypeptide and comprising specific embodiments of CARs are provided below.

In another aspect, provided herein are methods of treating an individual having a disease or disorder, wherein the disease or disorder is characterized, or is characterizable, by cells expressing an antigen, comprising administering to the individual cells, e.g., T lymphocytes, expressing a polypeptide, as described herein. In certain embodiments, when the modified cells, e.g., modified T lymphocytes described herein are administered to a subject in need thereof, the combination of multimerizing agent and cell death polypeptide selected are chosen such that they are compatible with the patient population (or subpopulation) in which the cells, e.g., T lymphocytes, have been administered. By way of example only, if the multimerizing agent selected is the antibody rituximab, then in certain embodiments the patient population is individuals having a cancer of the B cells, e.g., B cell lymphoma.

4. DETAILED DESCRIPTION

4.1. Cells Comprising Cell Death Polypeptides

Provided herein are genetically modified cells, for example immune cells, such as T lymphocytes, e.g., human T lymphocytes, that comprise an artificial multimerizable, e.g., dimerizable, polypeptide (referred to herein as a "cell death polypeptide") that, when multimerized, e.g., dimerized, by a multimerizing agent, e.g., dimerizing agent, generates an apoptosis-inducing signal in a cell, e.g., a T lymphocyte, that expresses the polypeptide, resulting in cell death, e.g., via apoptosis. Without wishing to be bound by any particular mechanism or theory, it is thought that when a sufficient number of a plurality of cell death polypeptides of the cell are multimerized, e.g., dimerized, that the aggregate apoptosis-inducing signal thereby generated is sufficient to kill the cell, e.g., cause the cell to undergo apoptosis. In a specific embodiment, the genetically modified cells provided herein are T lymphocytes.

In certain embodiments, the cell death polypeptide can be multimerized or dimerized by an administrable multimerizing agent or dimerizing agent, e.g., a protein (e.g., antibody, receptor or ligand-binding portion thereof, a ligand or receptor-binding portion thereof), oligonucleotide, or the like. In certain embodiments, the multimerizing agent is not a small molecule. The multimerizing or dimerizing agent can be used to kill T lymphocytes comprising the cell death polypeptide either in vitro or in vivo.

Thus, in a first aspect, provided herein is a T lymphocyte comprising an artificial polypeptide (cell death polypeptide) comprising an apoptosis-inducing domain, wherein said cell death polypeptide is multimerizable using a multimerizing agent, wherein said multimerizing agent is not an FK506 binding protein (FKBP) ligand, and wherein when said multimerizing agent multimerizes said polypeptide, an apoptosis-inducing signal is generated in said T lymphocyte. In a specific embodiment, said multimerizing agent is a dimerizing agent; that is, the multimerizing agent causes the cell death polypeptide to dimerize. In another specific embodiment, when said dimerizing agent dimerizes said cell death polypeptide, an apoptosis-inducing signal is generated in said T lymphocyte. The cell death polypeptide does not comprise an FK506 binding protein, functional portion thereof, or modified form thereof.

In certain embodiments, said cell death polypeptide is a transmembrane polypeptide comprising an extracellular domain, a transmembrane domain, and an intracellular domain comprising said apoptosis-inducing domain. In certain embodiments, the apoptosis-inducing domain of the cell death polypeptide can be, for example, any protein or portion thereof that when dimerized initiates an apoptosis-inducing signal in the cell. In certain embodiments, the apoptosis-inducing domain is any caspase that homodimerizes, and preferably is or comprises a caspase, e.g., caspase 9, caspase 8, or caspase 3 (e.g., human caspase 9, caspase 8, or caspase 3). The amino acid sequences of human caspases, including human caspase 9, human caspase 8, and human caspase 3 are well known in the art. For example, human caspase 3 has been assigned NCBI Gene ID: 836; human caspase 8 has been assigned NCBI Gene ID: 841; and human caspase 9 has been assigned NCBI Gene ID: 842. In certain embodiments, the intracellular domain that is, or comprises, a caspase domain, and the extracellular domain, which comprises the epitope or mimotope, are joined by a CD8α stalk or CD8β stalk, at least part of which can function as a transmembrane domain.

In certain embodiments, the dimerizing agent is a polypeptide comprising at least two sites that specifically bind to a cell death polypeptide, e.g., an extracellular domain of a cell death polypeptide. In particular embodiments, the polypeptide is an antibody, e.g., an antibody comprising at least two epitope or mimotope binding sites. In certain embodiments, only the antigen binding domain of an antibody is used as a multimerizing or dimerizing agent. In certain embodiments, an extracellular domain of a cell death polypeptide comprises at least one epitope or mimotope to which the antibody specifically binds. In particular embodiments, the antibody is a bispecific antibody comprising two different epitope or mimotope binding sites that bind two different epitopes or mimotopes present on an extracellular domain of a cell death polypeptide. In certain embodiments, the antibody is an IgG or an IgM antibody. Artificial antibody constructs comprising epitope-binding or mimotope-binding domains from antibodies, optionally joined by one or more linkers, may also be used.

In a specific embodiment, said antibody, useful as a multimerizing or dimerizing agent, has been approved by a governmental regulatory authority, e.g., the United States Food and Drug Administration for any use. This ensures, e.g., that the antibody, when used as a dimerizing or multimerizing agent, has a known toxicity and patient safety profile. Any combination of antibody and associated target may be used in the T lymphocytes provided herein. In one embodiment, an antibody useful as a multimerizing or dimerizing agent is one that specifically binds to a CD20 epitope or mimotope, e.g., a human CD20 epitope or mimotope, and an extracellular domain of a cell death polypeptide comprises a CD20 epitope or mimotope to which the antibody specifically binds. In certain specific embodiments, the antibody is rituximab and an extracellular domain of a cell death polypeptide comprises a CD20 epitope or a CD20 mimotope that specifically binds to said rituximab. In another specific embodiment, the antibody is tositumumab and an extracellular domain of a cell death polypeptide comprises a CD20 epitope or a CD20 mimotope that specifically binds to said tositumumab. In yet another embodiment, the antibody is ibritumomab and an extracellular domain of a cell death polypeptide comprises a CD20 epitope or a CD20 mimotope that specifically binds to said ibritumomab. In still another embodiment, the antibody is ofatumumab and an extracellular domain of a cell death polypeptide comprises a CD20 epitope or a CD20 mimotope that specifically binds to said atumumab.

In another specific embodiment, the antibody is alemtuzumab and an extracellular domain of a cell death polypeptide comprises a CD52 epitope or a CD52 mimotope that specifically binds to said alemtuzumab. In yet another embodiment, the antibody is basiliximab and an extracellular domain of the cell death polypeptide comprises a CD25 epitope or a CD25 mimotope that specifically binds to said basiliximab. In another embodiment, the antibody is daclizumab and an extracellular domain of a cell death polypeptide comprises a CD25 epitope or a CD25 mimotope that specifically binds to said daclizumab. In still another embodiment, the antibody is brentuximab and an extracellular domain of a cell death polypeptide comprises a CD30 epitope or a CD30 mimotope that specifically binds to said brentuximab. In another embodiment, the antibody is belimumab and an extracellular domain of a cell death polypeptide comprises a B-cell activating factor (BAFF) epitope or a BAFF mimotope that specifically binds to said belimumab. In another embodiment, the antibody is cetuximab and an extracellular domain of a cell death polypeptide comprises an epidermal growth factor receptor (EGFR) epitope or an EGFR mimotope that specifically binds to said cetuximab. In yet another embodiment, the antibody is panitumumab and an extracellular domain of a cell death polypeptide comprises an epidermal growth factor receptor (EGFR) epitope or an EGFR mimotope that specifically binds to said panitumumab. In another embodiment, the antibody is efalizumab and an extracellular domain of a cell death polypeptide comprises an epitope of CD11a or a mimotope of CD11a that specifically binds to said efalizumab. In still another embodiment, the antibody is ipilimumab and an extracellular domain of a cell death polypeptide comprises a CD152 epitope or CD152 mimotope that specifically binds to said ipilimumab. In still another embodiment, the antibody is natalizumab and an extracellular domain of a cell death polypeptide comprises an epitope of alpha-4 integrin or a mimotope of alpha 4 integrin that specifically binds to said natalizumab. In another embodiment, the antibody is basiliximab and an extracellular domain of a cell death polypeptide comprises a CD25 epitope or CD25 mimotope that specifically binds to said basiliximab.

Ligands and receptors can be utilized in the construction of the cell death polypeptides provided herein, and multimerizing agents or dimerizing agents comprising the receptors' respective ligands can be used to multimerize or dimerize the polypeptides. In certain embodiments, when a multimerizing agent or a dimerizing agent binds to at least two cell death polypeptides, dimerization or multimerization of the cell death polypeptides occurs, e.g., dimerization or multimerization of the cell death polypeptides occurs. In certain embodiments, an extracellular domain of a cell death polypeptide is or comprises a receptor or a ligand-binding portion thereof. In a specific embodiment, a multimerizing agent or dimerizing agent is or comprises at least two ligands for said receptor or ligand binding portion thereof. In another specific embodiment, said multimerizing agent or dimerizing agent binds to said receptor or said ligand binding portion thereof on two of the cell death polypeptides, and said polypeptides are multimerized or dimerized, e.g., the intracellular domains of said polypeptides are multimerized or dimerized. In particular embodiments the cell death polypeptides comprise intracellular domains comprising a caspase domain, and multimerization or dimerization of the caspase domains occurs. In specific embodiments, said multimerization or dimerization, for example, multimerization or dimerization of intracellular domains, e.g., multimerization or dimerization of caspase domains, initiates an apoptosis-inducing signal in said cell, e.g., T lymphocyte.

In specific embodiments, when an antibody specifically binds to an epitope or mimotope of at least two cell death polypeptides, dimerization of the cell death polypeptides occurs, e.g., dimerization of the intracellular domains of the cell death polypeptides occurs. In particular embodiments the cell death polypeptides comprise intracellular domains comprising a caspase domain, and dimerization of the caspase domains occurs. In specific embodiments, said dimerization, for example, dimerization of intracellular domains, e.g., dimerization of caspase domains, initiates an apoptosis-inducing signal in said cell, e.g., T lymphocyte.

In certain other embodiments of the cell, e.g., T lymphocyte, said extracellular domain of the cell death polypeptide comprises a ligand for a receptor. In a specific embodiment, said multimerizing agent or dimerizing agent comprises at least two receptors or ligand-binding portions thereof that bind to said ligand. In a specific embodiment, when said multimerizing agent or dimerizing agent binds to said receptor or said ligand binding portion thereof on at least two of the cell death polypeptides, said polypeptides are multimerized or dimerized. In a specific embodiment, when the cell death polypeptides are multimerized or dimerized, an apoptosis-inducing signal is generated in said cell. In a specific embodiment, said cell is a T lymphocyte.

In certain other embodiments, an extracellular domain of a cell death polypeptide comprises an artificial oligonucleotide sequence. For example, in particular embodiments, a modified cell, e.g., T lymphocyte, comprises a cell death polypeptide comprising an extracellular domain that comprises an artificial oligonucleotide sequence. In a specific embodiment, a multimerizing or dimerizing agent is or comprises at least one multimerizing or dimerizing oligonucleotide comprising a first oligonucleotide and a second oligonucleotide, optionally joined by a linker, wherein said first oligonucleotide and said second oligonucleotide are complementary to said artificial oligonucleotide sequence. In certain specific embodiments, said first oligonucleotide and said second oligonucleotide have the same sequence. In specific embodiments, said first oligonucleotide and said second oligonucleotide are joined in a head-to-head or tail-to-tail conformation. In specific embodiments, when said multimerizing or dimerizing oligonucleotide of said multimerizing agent or dimerizing agent hybridizes to the artificial oligonucleotide sequence of two of said cell death polypeptides, the cell death polypeptides are multimerized or dimerized. In another specific embodiment, when the cell death polypeptides are multimerized or dimerized, an apoptosis-inducing signal is generated in said cell. In particular embodiments, the cell death polypeptides comprise intracellular caspase domains, and when the intracellular caspase domains are multimerized or dimerized, an apoptosis-inducing signal is generated in said cell. In a specific embodiment, said cell is a T lymphocyte.

In certain other embodiments of the T lymphocyte, the multimerizing or dimerizing agent is an artificial polypeptide comprising two or more binding domains joined by one or more linkers.

In a specific embodiment, provided herein is a cell, e.g., a T lymphocyte, comprising a cell death polypeptide comprising an extracellular domain comprising an epitope, a transmembrane domain, and an intracellular domain comprising a caspase 9, e.g., a human caspase 9, or a functional portion thereof. In another specific embodiment, provided herein is a cell, e.g., a T lymphocyte, comprising an artificial polypeptide comprising an extracellular domain comprising a receptor or ligand-binding portion thereof, and an intracellular domain comprising a caspase 9, e.g., a human caspase 9, or a functional portion thereof. In another specific embodiment, provided herein is a cell, e.g., a T lymphocyte, comprising an artificial polypeptide comprising an extracellular domain comprising a ligand or a receptor-binding portion thereof, wherein said ligand binds a receptor or ligand-binding portion thereof, and an intracellular domain comprising a caspase 9, e.g., a human caspase 9, or functional portion thereof. In a specific embodiment, said cell is a T lymphocyte.

In any of the embodiments herein, wherein the modified cells are T lymphocytes, the T lymphocytes may be CD4+T lymphocytes or CD8+T lymphocytes. The T lymphocytes may be, without genetic modification, specific for a particular antigen (e.g., a tumor-associated antigen, tumor-specific antigen, viral antigen, or the like). The T lymphocytes may be genetically modified to express one or more polypeptides, e.g., chimeric antigen receptors, that target the T lymphocyte to a specific antigen.

4.2. Methods of Killing Cells that Comprise Cell Death Polypeptides

The cell death polypeptides provided herein can be used in methods of killing cells, e.g., T lymphocytes, that comprise the cell death polypeptides. The cell death polypeptides provided herein may be used in conjunction with any cells, in particular, any mammalian cells, for example, any human cells. Such cell death polypeptides provide, for example, a useful safety feature for cell therapeutics. As such, the cell death polypeptides can, for example, be important for a drug product comprising a cell therapeutic, e.g., a chimeric antigen receptor-expressing CAR T lymphocytes, because the cell death polypeptides enable rapid killing of the cell therapeutic, e.g., the T lymphocytes, should such rapid killing become desirable, e.g., in the event administration of the cells causes any unwanted or deleterious effects in a patient receiving them, or if the presence of the cell therapeutic, e.g., the T lymphocytes, in a subject is no longer necessary. Thus, in certain embodiments, the cell death polypeptides provided herein can be used in conjunction with any administrable cells, for example cell therapeutics, such as mammalian cell therapeutics, e.g., human cell therapeutics. Non-limiting examples of cells in which the cell death polypeptides and multimerizing or dimerizing agents may be used include, but are not limited to, natural killer (NK) cells, dendritic cells (DC), placental stem cells (e.g., the placental stem cells disclosed in U.S. Pat. Nos. 7,468,276; 8,057,788 and 8,202,703, the disclosures of which are hereby incorporated by reference in their entireties), mesenchymal-like stem cells from umbilical cord blood, placental blood, peripheral blood, bone marrow, dental pulp, adipose tissue, osteochondral tissue, and the like; embryonic stem cells, embryonic germ cells, neural crest stem cells, neural stem cells, and differentiated cells (e.g., fibroblasts, etc.). The cell death polypeptides, and multimerizing or dimerizing agents, may also be used in tumor cell lines, e.g., for animal model experimental purposes.

Cell killing by the cell death polypeptides described herein can take place either in vivo, e.g., in an individual to whom the cells, e.g., T lymphocytes, have been administered, or in vitro, e.g., in a laboratory, e.g., as part of quality control experiments. In one embodiment, provided herein is a method of killing a cell, e.g., a T lymphocyte, wherein said cell comprises a plurality of artificial cell death polypeptides each comprising an apoptosis-inducing domain, wherein said polypeptides are multimerizable or dimerizable using a multimerizing agent or dimerizing agent that is not an FK506 binding protein (FKBP) ligand, and wherein when said multimerizing agent or dimerizing agent multimerizes or dimerizes said polypeptide, an apoptosis-inducing signal is generated in said cell, comprising contacting said cell with an amount of said multimerizing agent or dimerizing agent sufficient for said plurality of artificial polypeptides to dimerize and generate an aggregate apoptosis-inducing signal sufficient to kill said cell. In certain embodiments, the cell death polypeptide is a transmembrane polypeptide comprising an extracellular domain, a transmembrane domain, and an intracellular domain comprising said apoptosis-inducing domain. In certain embodiments, the intracellular domain that is, or comprises, a caspase domain, and the extracellular domain, which comprises the epitope or mimotope, are joined by a CD8α stalk or CD8β stalk, at least part of which can function as a transmembrane domain. In certain specific embodiments of the method, the apoptosis-inducing domain of said polypeptide is or comprises a caspase, e.g., caspase 3, caspase 8, or caspase 9 (e.g., human caspase 9, caspase 8, or caspase 3).

The multimerizing agent or dimerizing agent used in the method can be any compound, other than a small molecule, that can dimerize or multimerizes a cell death polypeptide, e.g., a protein, an oligonucleotide or a polysaccharide. In certain embodiments, the multimerizing agent or dimerizing agent is an antibody, e.g., an antibody that comprises at least two epitope-binding sites or at least two mimotope-binding sites. In certain embodiments, only the antigen binding domain of an antibody is used as a multimerizing or dimerizing agent. In such embodiments, the extracellular domain of the cell death polypeptide comprises an epitope or mimotope to which the antibody binds. The antibody can be an antibody of any valence, but is preferably an IgG or an IgM antibody.

In a specific embodiment, said antibody, useful as a multimerizing or dimerizing agent, has been approved by a governmental regulatory authority, e.g., the United States Food and Drug Administration for any use. Any combination of antibody and associated target may be used in the methods of killing T lymphocytes provided herein.

In a specific embodiment, when the multimerizing agent or dimerizing agent is an antibody, said antibody is one that specifically binds to a CD20 epitope or mimotope, e.g., a human CD20 epitope or mimotope, and said extracellular domain of a cell death polypeptide comprises a CD20 epitope or mimotope to which said antibody specifically binds. In certain specific embodiments, when the multimerizing agent or dimerizing agent is an antibody, said antibody is rituximab and said extracellular domain of the cell death polypeptide comprises a CD20 epitope or a CD20 mimotope that binds to said rituximab; said antibody is tositumumab and said extracellular domain of the cell death polypeptide comprises a CD20 epitope or a CD20 mimotope that binds to said tositumumab; said antibody is ibritumomab and said extracellular domain of the cell death polypeptide comprises a CD20 epitope or a CD20 mimotope that binds said ibritumomab; said antibody is ofatumomab and said extracellular domain of the cell death polypeptide comprises a CD20 epitope or a CD20 mimotope that binds said ofatumumab; or said antibody is alemtuzumab and said extracellular domain of the cell death polypeptide comprises a CD52 epitope or a CD52 mimotope that binds to said alemtuzumab.

In certain specific embodiments, when the multimerizing agent or dimerizing agent is an antibody, said antibody is said antibody is basiliximab and said extracellular domain of the cell death polypeptide comprises a CD25 epitope or a CD25 mimotope that binds said basiliximab; said antibody is daclizumab and said extracellular domain of the cell death polypeptide comprises a CD25 epitope or a CD25 mimotope that binds said daclizumab; said antibody is brentuximab and said extracellular domain of the cell death polypeptide comprises a CD30 epitope or a CD30 mimotope that binds said brentuximab; said antibody is belimumab and said extracellular domain of the cell death polypeptide comprises a B-cell activating factor (BAFF) epitope or a BAFF mimotope that binds said belimumab; said antibody is cetuximab and said extracellular domain of the cell death polypeptide comprises an epidermal growth factor receptor (EGFR) epitope or an EGFR mimotope that binds said cetuximab; said antibody is panitumumab and said extracellular domain of the cell death polypeptide comprises an epidermal growth factor receptor (EGFR) epitope or an EGFR mimotope that binds said panitumumab; said antibody is efalizumab and said extracellular domain of the cell death polypeptide comprises an epitope of CD11a or a mimotope of CD11a that binds to said efalizumab; said antibody is ipilimumab and said extracellular domain of the cell death polypeptide comprises a CD152 epitope or CD152 mimotope that binds said ipilimumab; said antibody is natalizumab and said extracellular domain of the cell death polypeptide comprises an epitope of alpha-4 integrin or a mimotope of alpha 4 integrin that binds said natalizumab; or said antibody is basiliximab and said extracellular domain of the cell death polypeptide comprises a CD25 epitope or CD25 mimotope that binds said basiliximab.

In a specific embodiment of any of the above embodiments, when said antibody binds to said epitope or mimotope on at least two of said cell death polypeptides, the intracellular domains of said polypeptides, and/or the respective caspases in said intracellular domains multimerize or dimerize. In specific embodiments, when said antibody specifically binds to an epitope or mimotope of at least two cell death polypeptides, dimerization of the cell death polypeptides occurs, e.g., dimerization of the intracellular domains of the cell death polypeptides occurs. In particular embodiments the cell death polypeptides comprise intracellular domains comprising a caspase domain, and dimerization of the caspase domains occurs. In specific embodiments, said dimerization, for example, dimerization of intracellular domains, e.g., dimerization of caspase domains, initiates an apoptosis-inducing signal in said cell, e.g., T lymphocyte.

Without intending to be limited by theory, when the antibody binds to the respective epitopes or mimotopes on at least two of said polypeptides, the intracellular domains of said polypeptides multimerizes, e.g., dimerize, at which time the respective caspases in said intracellular domains dimerize. Dimerization of said polypeptides initiates an apoptosis-inducing signal in said T lymphocyte.

As above, receptors and their respective ligands may be used to multimerize or dimerize cell death polypeptides, and thereby effect killing of a cell, e.g., a T lymphocyte, comprising the polypeptide. For example, the extracellular domain of said cell death polypeptide is or comprises a receptor or a ligand-binding portion thereof. In such embodiments, the multimerizing agent or dimerizing agent comprises at least two ligands for said receptor or ligand binding portion thereof, enabling multimerization or dimerization of the cell death polypeptide when the multimerizing agent or dimerizing agent binds to said receptor or said ligand binding portion thereof on at least two of said polypeptides, said polypeptides are dimerized. In preferred embodiments, dimerization of said polypeptides initiates an apoptosis-inducing signal in said cell.

In other embodiments of the method of killing cells, e.g., T lymphocytes, the extracellular domain of the cell death polypeptide comprises a ligand for a receptor. In such embodiments of the method, the multimerizing agent or dimerizing agent comprises at least two receptors or ligand-binding portions thereof that bind to said ligand. When the multimerizing dimerizing agent binds to said receptor or said ligand binding portion thereof on two of said cell death polypeptides, the intracellular domains, and thus preferably the caspase domains, in said polypeptides are dimerized. Dimerization of said intracellular domains, and the caspase domains, preferably initiates an apoptosis-inducing signal is generated in said cell.

In certain other embodiments of the method of killing cells, e.g., T lymphocytes, said extracellular domain of said cell death polypeptide comprises an artificial oligonucleotide sequence. For example, in particular embodiments, said cell death polypeptide comprises an extracellular domain that comprises an artificial oligonucleotide sequence. In a specific embodiment, a multimerizing or dimerizing agent is or comprises at least one multimerizing or dimerizing oligonucleotide comprising a first oligonucleotide and a second oligonucleotide, optionally joined by a linker, wherein said first oligonucleotide and said second oligonucleotide are complementary to said artificial oligonucleotide sequence. In certain specific embodiments, said first oligonucleotide and said second oligonucleotide have the same sequence. In specific embodiments, said first oligonucleotide and said second oligonucleotide are joined in a head-to-head or tail-to-tail conformation. In specific embodiments, when said multimerizing or dimerizing oligonucleotide of said multimerizing agent or dimerizing agent hybridizes to the artificial oligonucleotide sequence of two of said cell death polypeptides, the cell death polypeptides are multimerized or dimerized. In another specific embodiment, when the cell death polypeptides are multimerized or dimerized, an apoptosis-inducing signal is generated in said cell. In particular embodiments, the cell death polypeptides comprise intracellular caspase domains, and when the intracellular caspase domains are multimerized or dimerized, an apoptosis-inducing signal is generated in said cell. In a specific embodiment, said cell is a T lymphocyte.

In certain other embodiments of the method of killing T lymphocytes, the multimerizing or dimerizing agent is an artificial polypeptide comprising two or more binding domains joined by one or more linkers.

In a specific embodiment, provided herein is a method of killing a cell, e.g., a T lymphocyte, wherein said cell comprises a plurality of artificial cell death polypeptides each comprising a caspase or functional portion thereof, wherein said caspase is caspase 3, caspase 8 or caspase 9 (e.g., human caspase 3, caspase 8, or caspase 9), and, wherein said cell death polypeptide is dimerizable using an antibody, and wherein when said antibody dimerizes said polypeptide, an apoptosis-inducing signal is generated in said cell, comprising contacting said cell with an amount of said antibody sufficient to dimerize a sufficient number of said plurality of artificial polypeptides to dimerize and generate an aggregate apoptosis-inducing signal sufficient to kill said cell. In a specific embodiment, said cell is a T lymphocyte.

In another specific embodiment, provided herein is a method of killing a cell, e.g., a T lymphocyte, wherein said cell comprises a plurality of artificial cell death polypeptides each comprising a caspase or functional portion thereof, wherein said caspase is caspase 3, caspase 8 or caspase 9 (e.g., human caspase 3, caspase 8, or caspase 9), and, wherein said plurality of artificial polypeptides each comprises an extracellular domain comprising a receptor or ligand-binding portion thereof that bind a ligand, wherein said polypeptide is dimerizable using a dimerizing agent comprising two said ligands, and wherein when said dimerizing agent dimerizes two of said polypeptides, an apoptosis-inducing signal is generated in cell, comprising contacting said cell with an amount of said dimerizing agent sufficient to dimerize a sufficient number of said plurality of artificial cell death polypeptides to dimerize and generate an aggregate apoptosis-inducing signal sufficient to kill said cell. In a specific embodiment, said cell is a T lymphocyte.

In another specific embodiment, provided herein is a method of killing a cell, e.g., a T lymphocyte, wherein said cell comprises a plurality of artificial cell death polypeptides each comprising a caspase or functional portion thereof, wherein said caspase is caspase 3, caspase 8 or caspase 9 (e.g., human caspase 3, caspase 8, or caspase 9), and, wherein said plurality of artificial polypeptides each comprises an extracellular domain comprising a ligand or receptor-binding portion thereof that bind a receptor or ligand-binding portion thereof, wherein said polypeptides are dimerizable using a dimerizing agent comprising two said receptors or ligand-binding portion thereof, and wherein when said dimerizing agent dimerizes two of said polypeptides, an apoptosis-inducing signal is generated in said cell, comprising contacting said cell with an amount of said dimerizing agent sufficient to dimerize a sufficient number of said plurality of artificial polypeptides to dimerize and generate an aggregate apoptosis-inducing signal sufficient to kill said cell. In a specific embodiment, said cell is a T lymphocyte.

In another specific embodiment, provided herein is method of killing a cell, e.g., a T lymphocyte, wherein said cell comprises a plurality of artificial cell death polypeptides each comprising a caspase or functional portion thereof, wherein said caspase is caspase 3, caspase 8 or caspase 9 (e.g., human caspase 3, caspase 8, or caspase 9), and, wherein said plurality of artificial polypeptides each comprising an extracellular domain comprising an artificial oligonucleotide, wherein said plurality of polypeptides are dimerizable using a dimerizing agent comprising an oligonucleotide comprising a first oligonucleotide and a second oligonucleotide, wherein said first oligonucleotide and said second oligonucleotide have the same nucleotide sequence, and wherein said first oligonucleotide and second oligonucleotide optionally are joined by a linker, and wherein said first oligonucleotide and said second oligonucleotide are complementary to said artificial oligonucleotide in said extracellular domain of said polypeptide, and wherein when said dimerizing agent dimerizes two of said cell death polypeptides, an apoptosis-inducing signal is generated in said cell, comprising contacting said cell with an amount of said dimerizing agent sufficient to dimerize a sufficient number of said plurality of artificial polypeptides to dimerize and generate an aggregate apoptosis-inducing signal sufficient to kill said cell. In a specific embodiment, said cell is a T lymphocyte.

In a specific embodiment, the T lymphocytes killed in accordance with the methods described herein are CAR-T lymphocytes.

4.3. Chimeric Antigen Receptors

When the cells provided herein are T lymphocytes which comprise the cell death polypeptides described above, such T lymphocytes can, in certain embodiments, comprise chimeric antigen receptors (CARs), which are artificial membrane-bound proteins that direct a T lymphocyte to an antigen, and stimulate the T lymphocyte to kill a cell displaying the antigen. See, e.g., Eshhar, U.S. Pat. No. 7,741,465. At a minimum, the CAR comprises an extracellular domain that binds to an antigen, e.g., an antigen on a cell, a transmembrane domain, and an intracellular (cytoplasmic) signaling domain that transmits a primary activation signal to an immune cell. All other conditions being satisfied, when the CAR is expressed on the surface of, e.g., a T lymphocyte, and the extracellular domain of the CAR binds to an antigen, the intracellular signaling domain transmits a signal to the T lymphocyte to activate and/or proliferate, and, if the antigen is present on a cell surface, to kill the cell expressing the antigen. Because T lymphocytes require two signals, a primary activation signal and a costimulatory signal, in order to activate, typically CARs also comprise a costimulatory domain such that binding of the antigen to the extracellular domain results in transmission of both a primary activation signal and a costimulatory signal.

4.3.1. General CAR Structure Intracellular Domain

In certain embodiments, the intracellular domain of the CAR is or comprises an intracellular domain or motif of a protein that is expressed on the surface of T lymphocytes and triggers activation and/or proliferation of said T lymphocytes. Such a domain or motif is able to transmit a primary antigen-binding signal that is necessary for the activation of a T lymphocyte in response to the antigen's binding to the CAR's extracellular portion. Typically, this domain or motif comprises, or is, an ITAM (immunoreceptor tyrosine-based activation motif). ITAM-containing polypeptides suitable for CARs include, for example, the zeta CD3 chain (CD3ζ) or ITAM-containing portions thereof. In a specific embodiment, the intracellular domain is a CD3ζ intracellular signaling domain. In other specific embodiments, the intracellular domain is from a lymphocyte receptor chain, a TCR/CD3 complex protein, an Fc receptor subunit or an IL-2 receptor subunit.

In certain embodiments, the CAR additionally comprises one or more co-stimulatory domains or motifs, e.g., as part of the intracellular domain of the polypeptide. The one or more co-stimulatory domains or motifs can be, or comprise, one or more of a co-stimulatory CD27 polypeptide sequence, a co-stimulatory CD28 polypeptide sequence, a co-stimulatory OX40 (CD134) polypeptide sequence, a co-stimulatory 4-1BB (CD137) polypeptide sequence, or a co-stimulatory inducible T-cell costimulatory (ICOS) polypeptide sequence, or other costimulatory domain or motif.

The transmembrane region can be any transmembrane region that can be incorporated into a functional CAR, typically a transmembrane region from a CD4 or a CD8 molecule.

4.3.2. CAR Transmembrane Domains From CTLA4 or PD-1

In certain embodiments, the transmembrane domain of the CAR is from an immune system protein that normally transmits an inhibitory signal to such immune system cells, e.g., a transmembrane domain from CTLA4 (Cytotoxic T-Lymphocyte Antigen 4 or Cytotoxic T-Lymphocyte Associated protein 4) or PD-1 (Programmed Death-1).

In certain embodiments, any of the T lymphocytes provided herein, which comprise a plurality of cell death polypeptides, comprise a transmembrane domain from CTLA4 or PD-1 (Programmed Cell Death 1) In a specific embodiment, a T lymphocyte expressing said polypeptide, or any of such polypeptides described herein, is activated or stimulated to proliferate when said polypeptide binds to said antigen. In a specific embodiment, the polypeptide, when expressed on the surface of a T lymphocyte, directs the T lymphocyte to kill a cell expressing said antigen.

In specific embodiments of any of the polypeptides herein, in which the transmembrane domain of the polypeptide is from CTLA4, the CTLA4 transmembrane domain is from a mammalian CTLA4, e.g., human, primate, or rodent, e.g., murine CTLA4. Preferably, the transmembrane domain does not comprise amino acids from the intracellular domain, extracellular domain, or either intracellular or extracellular domain of CTLA4 or PD-1. Specific, non-limiting examples of CTLA4 or PD-1 transmembrane domain sequences are provided below.

In a specific embodiment, the CTLA4 transmembrane domain is the polypeptide sequence encoded by exon 3 of a human CTLA4 gene. In another specific embodiment, the CTLA4 transmembrane domain is or comprises the amino acid sequence PEPCPDSDFLLWILAAVSSGLFFYSFLL-TAVSLSKM (in three-letter code, Pro-Glu-Pro-Cys-Pro-Asp-Ser-Asp-Phe-Leu-Leu-Trp-Ile-Leu-Ala-Ala-Val-Ser-Ser-Gly-Leu-Phe-Phe-Tyr-Ser-Phe-Leu-Leu-Thr-Ala-Val-Ser-Leu-Ser-Lys-Met) (SEQ ID NO:1). In another specific embodiment, the CTLA4 transmembrane domain is or comprises the polypeptide sequence encoded by nucleotides 610-722 of GenBank Accession No. NM_005214.4. In another specific embodiment, the CTLA4 transmembrane domain is or comprises the amino acid sequence PDSD-FLLWILAAVSSGLFFYSFLLTAVSL (in three-letter code, Pro-Asp-Ser-Asp-Phe-Leu-Leu-Trp-Ile-Leu-Ala-Ala-Val-Ser-Ser-Gly-Leu-Phe-Phe-Tyr-Ser-Phe-Leu-Leu-Thr-Ala-Val-Ser-Leu) (SEQ ID NO:2). In another specific embodiment, the CTLA4 transmembrane domain is or comprises the polypeptide sequence encoded by nucleotides 636-699 of GenBank Accession No. NM_005214.4. In another specific embodiment, the CTLA4 transmembrane domain is or comprises the amino acid sequence FLLWILAAVSS-GLFFYSFLLTAV (in three-letter code, Phe-Leu-Leu-Trp-Ile-Leu-Ala-Ala-Val-Ser-Ser-Gly-Leu-Phe-Phe-Tyr-Ser-Phe-Leu-Leu-Thr-Ala-Val) (SEQ ID NO:3). See, e.g., Ensembl protein reference no. ENSP00000303939.3. In another specific embodiment, the CTLA4 transmembrane domain is or comprises the polypeptide sequence FLLWI-LAAVSSGLFFYSFLLT (in three-letter code, Phe-Leu-Leu-Trp-Ile-Leu-Ala-Ala-Val-Ser-Ser-Gly-Leu-Phe-Phe-Tyr-Ser-Phe-Leu-Leu-Thr) (SEQ ID NO:4), see, e.g., UNIPROT Accession No. P16410. In another specific embodiment, the CTLA4 transmembrane domain is or comprises the polypeptide sequence FLLWILVAVSLGLFFYSFLVSAVSLS (in three-letter code, Phe-Leu-Leu-Trp-Ile-Leu-Val-Ala-Val-Ser-Leu-Gly-Leu-Phe-Phe-Tyr-Ser-Phe-Leu-Val-Ser-Ala-Val-Ser-Leu-Ser) (SEQ ID NO:5). See, e.g., Shin et al., *Blood* 119:5678-5687 (2012). In another specific embodiment, the PD-1 transmembrane domain is or comprises the amino acid sequence TLVVGVVGGLLGSLVLLVWV-LAVICSRAA (in three-letter code, Thr-Leu-Val-Val-Gly-Val-Val-Gly-Gly-Leu-Leu-Gly-Ser-Leu-Val-Leu-Leu-Val-Trp-Val-Leu-Ala-Val-Ile-Cys-Ser-Arg-Ala-Ala) (SEQ ID NO:6). See Finger et al., *Gene* 197(1-2):177-187 (1997). In another specific embodiment, the PD-1 transmembrane domain is or comprises the amino acid sequence VGVVG-GLLGSLVLLVWVLAVI (in three-letter code, Val-Gly-Val-Val-Gly-Gly-Leu-Leu-Gly-Ser-Leu-Val-Leu-Leu-Val-Trp-Val-Leu-Ala-Val-Ile) (SEQ ID NO:7). See, e.g., UNIPROT Accession No. Q15116. In another specific embodiment, the PD-1 transmembrane domain is or comprises the amino acid sequence FQTLVVGVVGGLLGSLVLLVWVLAVI (in three-letter code, Phe-Gln-Thr-Leu-Val-Val-Gly-Val-Val-Gly-Gly-Leu-Leu-Gly-Ser-Leu-Val-Leu-Leu-Val-Trp-Val-Leu-Ala-Val-Ile) (SEQ ID NO:8). See, e.g., GenBank Accession No. NM_005018.2. In certain embodiments, a nucleotide sequence that encodes one of the transmembrane polypeptides disclosed herein comprises a nucleotide sequence that encodes any of the amino acid sequences disclosed in SEQ ID NO:1, SEQ ID NO:2, SEQ ID NO:3, SEQ ID NO:4, SEQ ID NO:5, SEQ ID NO:6, SEQ ID NO:7 or SEQ ID NO:8. In another specific embodiment, the PD-1 transmembrane domain is or comprises at least 10, 11, 12, 13, 14, 15, 16, 17, 18, 19, 20 or 21 consecutive amino acids disclosed in SEQ ID NO:1, SEQ ID NO:2, SEQ ID NO:3, SEQ ID NO:4, SEQ ID NO:5, SEQ ID NO:6, SEQ ID NO:7 or SEQ ID NO:8. In certain embodiments, a nucleotide sequence that encodes one of the polypeptides disclosed herein comprises a nucleotide sequence that encodes at least 10, 11, 12, 13, 14, 15, 16, 17, 18, 19, 20 or 21 consecutive amino acids disclosed in SEQ ID NO:1, SEQ ID NO:2, SEQ ID NO:3, SEQ ID NO:4, SEQ ID NO:5, SEQ ID NO:6, SEQ ID NO:7 or SEQ ID NO:8. In constructing the polypeptide, e.g. CAR, in certain embodiments, human sequences may be combined with non-human sequences. For example, a polypeptide, e.g. CAR comprising human extracellular and intracellular domain amino acid sequences may comprise a transmembrane domain from a non-human species; e.g., may comprise a murine CTLA4 transmembrane domain or a murine PD-1 transmembrane domain. In a more specific embodiment, the polypeptide, e.g. CAR, comprises human amino acid sequences for the extracellular and intracellular domains, and comprises a transmembrane domain having, or consisting of, the amino acid sequence of SEQ ID NO:5.

4.3.3. CAR Intracellular Domain

The extracellular domain of the polypeptide binds to an antigen of interest. In certain embodiments of any of the polypeptides described herein, the extracellular domain comprises a receptor, or a portion of a receptor, that binds to said antigen. The extracellular domain may be, e.g., a receptor, or a portion of a receptor, that binds to said antigen. In certain embodiments, the extracellular domain comprises, or is, an antibody or an antigen-binding portion thereof. In specific embodiments, the extracellular domain comprises, or is, a single-chain Fv domain. The single-chain Fv domain can comprise, for example, a $V_L$ linked to $V_H$ by a flexible linker, wherein said $V_L$ and $V_H$ are from an antibody that binds said antigen.

The antigen to which the extracellular domain of the polypeptide binds can be any antigen of interest, e.g., can be an antigen on a tumor cell. The tumor cell may be, e.g., a cell in a solid tumor, or a cell of a blood cancer. The antigen can be any antigen that is expressed on a cell of any tumor or cancer type, e.g., cells of a lymphoma, a lung cancer, a breast cancer, a prostate cancer, an adrenocortical carcinoma, a thyroid carcinoma, a nasopharyngeal carcinoma, a melanoma, e.g., a malignant melanoma, a skin carcinoma, a colorectal carcinoma, a desmoid tumor, a desmoplastic small round cell tumor, an endocrine tumor, an Ewing sarcoma, a peripheral primitive neuroectodermal tumor, a solid germ cell tumor, a hepatoblastoma, a neuroblastoma, a non-rhabdomyosarcoma soft tissue sarcoma, an osteosarcoma, a retinoblastoma, a rhabdomyosarcoma, a Wilms tumor, a glioblastoma, a myxoma, a fibroma, a lipoma, or the like. In more specific embodiments, said lymphoma can be chronic lymphocytic leukemia (small lymphocytic lymphoma), B-cell prolymphocytic leukemia, lymphoplasmacytic lymphoma, Waldenström macroglobulinemia, splenic marginal zone lymphoma, plasma cell myeloma, plasmacytoma, extranodal marginal zone B cell lymphoma, MALT lymphoma, nodal marginal zone B cell lymphoma, follicular lymphoma, mantle cell lymphoma, diffuse large B cell lymphoma, mediastinal (thymic) large B cell lymphoma, intravascular large B cell lymphoma, primary effusion lymphoma, Burkitt's lymphoma, T lymphocyte prolymphocytic leukemia, T lymphocyte large granular lymphocytic leukemia, aggressive NK cell leukemia, adult T lymphocyte leukemia/lymphoma, extranodal NK/T lymphocyte lymphoma, nasal type, enteropathy-type T lymphocyte lymphoma, hepatosplenic T lymphocyte lymphoma, blastic NK cell lymphoma, mycosis fungoides, Sezary syndrome, primary cutaneous anaplastic large cell lymphoma, lymphomatoid papulosis, angioimmunoblastic T lymphocyte lymphoma, peripheral T lymphocyte lymphoma (unspecified), anaplastic large cell lymphoma, Hodgkin lymphoma, or a non-Hodgkin lymphoma.

In a specific embodiment, in which the cancer is chronic lymphocytic leukemia (CLL), the B cells of the CLL have a normal karyotype. In other specific embodiments, in which the cancer is chronic lymphocytic leukemia (CLL), the B cells of the CLL carry a 17p deletion, an 11q deletion, a 12q trisomy, a 13q deletion or a p53 deletion.

In certain embodiments, the antigen is a tumor-associated antigen or a tumor-specific antigen. In various specific embodiments, without limitation, the tumor-associated antigen or tumor-specific antigen is Her2, prostate stem cell antigen (PSCA), alpha-fetoprotein (AFP), carcinoembryonic antigen (CEA), cancer antigen-125 (CA-125), CA19-9, calretinin, MUC-1, epithelial membrane protein (EMA), epithelial tumor antigen (ETA), tyrosinase, melanoma-associated antigen (MAGE), CD19, CD34, CD45, CD99, CD117, chromogranin, cytokeratin, desmin, glial fibrillary acidic protein (GFAP), gross cystic disease fluid protein (GCDFP-15), HMB-45 antigen, protein melan-A (melanoma antigen recognized by T lymphocytes; MART-1), myo-D1, muscle-specific actin (MSA), neurofilament, neuron-specific enolase (NSE), placental alkaline phosphatase, synaptophysis, thyroglobulin, thyroid transcription factor-1, the dimeric form of the pyruvate kinase isoenzyme type M2 (tumor M2-PK), an abnormal ras protein, or an abnormal p53 protein.

In certain embodiments, the TAA or TSA is a cancer/testis (CT) antigen, e.g., BAGE, CAGE, CTAGE, FATE, GAGE, HCA661, HOM-TES-85, MAGEA, MAGEB, MAGEC, NA88, NY-ESO-1, NY-SAR-35, OY-TES-1, SPANXB1, SPA17, SSX, SYCP1, or TPTE.

In certain other embodiments, the TAA or TSA is a carbohydrate or ganglioside, e.g., fuc-GM1, GM2 (oncofetal antigen-immunogenic-1; OFA-I-1); GD2 (OFA-I-2), GM3, GD3, and the like.

In certain other embodiments, the TAA or TSA is alpha-actinin-4, Bage-1, BCR-ABL, Bcr-Abl fusion protein, beta-catenin, CA 125, CA 15-3 (CA 27.29\BCAA), CA 195, CA 242, CA-50, CAM43, Casp-8, cdc27, cdk4, cdkn2a, CEA, coa-1, dek-can fusion protein, EBNA, EF2, Epstein Barr virus antigens, ETV6-AML1 fusion protein, HLA-A2, HLA-A11, hsp70-2, KIAAO205, Mart2, Mum-1, 2, and 3, neo-PAP, myosin class I, OS-9, pml-RARα fusion protein, PTPRK, K-ras, N-ras, triosephosphate isomerase, Gage 3,4, 5,6,7, GnTV, Herv-K-mel, Lage-1, NA-88, NY-Eso-1/Lage-2, SP17, SSX-2, TRP2-Int2, gp100 (Pmel 17), tyrosinase, TRP-1, TRP-2, MAGE-1, MAGE-3, RAGE, GAGE-1, GAGE-2, p15(58), RAGE, SCP-1, Hom/Mel-40, PRAME, p53, H-Ras, HER-2/neu, E2A-PRL, H4-RET, IGH-IGK, MYL-RAR, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, 13-Catenin, Mum-1, p16, TAGE, PSMA, CT7, telomerase, 43-9F, 5T4, 791Tgp72, 13HCG, BCA225, BTAA, CD68\KP1, CO-029, FGF-5, G250, Ga733 (EpCAM), HTgp-175, M344, MA-50, MG7-Ag, MOV18, NB\70K, NY-CO-1, RCAS1, SDC-CAG16, TA-90, TAAL6, TAG72, TLP, TPS, CD19, CD22, CD27, CD30, CD70, GD2 (ganglioside G2), EGFRvIII (epidermal growth factor variant III), sperm protein 17 (Sp17), mesothelin, PAP (prostatic acid phosphatase), prostein, TARP (T cell receptor gamma alternate reading frame protein), Trp-p8, STEAP1 (six-transmembrane epithelial antigen of the prostate 1), an abnormal ras protein, or an abnormal p53 protein. In another specific embodiment, said tumor-associated antigen or tumor-specific antigen is integrin αvβ3 (CD61), galactin, K-Ras (V-Ki-ras2 Kirsten rat sarcoma viral oncogene), or Ral-B. Other tumor-associated and tumor-specific antigens are known to those in the art.

Antibodies, and scFvs, that bind to TSAs and TAAs are known in the art, as are nucleotide sequences that encode them.

In certain specific embodiments, the antigen is an antigen not considered to be a TSA or a TAA, but which is nevertheless associated with tumor cells, or damage caused by a tumor. In certain embodiments, for example, the antigen is, e.g., a growth factor, cytokine or interleukin, e.g., a growth factor, cytokine, or interleukin associated with angiogenesis or vasculogenesis. Such growth factors, cytokines, or interleukins can include, e.g., vascular endothelial growth factor (VEGF), basic fibroblast growth factor (bFGF), platelet-derived growth factor (PDGF), hepatocyte growth factor (HGF), insulin-like growth factor (IGF), or interleukin-8 (IL-8). Tumors can also create a hypoxic environment local to the tumor. As such, in other specific embodiments, the antigen is a hypoxia-associated factor, e.g., HIF-1α, HIF-1β, HIF-2α, HIF-2β, HIF-3α, or HIF-3β. Tumors can also cause localized damage to normal tissue, causing the release of molecules known as damage associated molecular pattern molecules (DAMPs; also known as alarmins). In certain other specific embodiments, therefore, the antigen is a DAMP, e.g., a heat shock protein, chromatin-associated protein high mobility group box 1 (HMGB1), S100A8 (MRP8, calgranulin A), S100A9 (MRP14, cal-granulin B), serum amyloid A (SAA), or can be a deoxyribonucleic acid, adenosine triphosphate, uric acid, or heparin sulfate.

In certain embodiments of the polypeptides described herein, the extracellular domain is joined to said transmembrane domain by a linker, spacer or hinge polypeptide sequence, e.g., a sequence from CD28 or a sequence from CTLA4.

4.3.4. Bispecific CARs

In certain embodiments of the T lymphocytes or methods described herein, the T lymphocytes, in addition to comprising a cell death polypeptide, comprise two or more CARs in which the primary signaling mechanism and costimulatory mechanism are split into two or more polypeptides.

In certain embodiments, for example, the T lymphocytes comprise a cell death polypeptide, and at least two different other polypeptides, e.g., chimeric receptors, in which the immune signal derived from binding of a primary signaling polypeptide, e.g., chimeric receptor, to a first antigen is separated from a costimulatory signal produced by a costimulatory polypeptide, e.g., chimeric receptor, wherein the costimulatory signal is dependent on antigen binding of a second antigen by the second chimeric receptor.

In one embodiment, the T lymphocyte comprises a primary signaling polypeptide comprising a first extracellular antigen binding domain that binds a first antigen, and a first intracellular signaling domain, wherein said primary signaling polypeptide does not comprise a co-stimulatory domain; and a co-stimulatory comprising a second extracellular antigen binding domain binding a second antigen, or a receptor that binds said second antigen; and a second intracellular signaling domain; wherein said T lymphocyte becomes maximally cytotoxic only when said first signaling domain and said second signaling domain are both activated by said first antigen and said second antigen, respectively. In a specific embodiment, binding of said first antigen to said first antigen binding domain without binding of said second antigen to said second binding domain, or binding of said second antigen to said second antigen binding domain without binding of first second antigen to said first binding domain, induces anergy of said T lymphocyte, or non-responsiveness of said T-lymphocyte to said first antigen or said second antigen.

In another specific embodiment, said first antigen binding domain and said second antigen binding domain are independently an antigen-binding portion of a receptor, an antigen-binding portion of an antibody, or other peptide-based macromolecular antigen binding agent. In certain specific embodiments, either or both of said first antigen binding domain or said second antigen binding domain are scFv antibody fragments. In specific embodiments, either or both of said primary signaling polypeptide or said co-stimulatory polypeptide additionally comprise a transmembrane domain. In other specific embodiments, said primary signaling polypeptide or said co-stimulatory polypeptide comprises a T lymphocyte survival motif. In a specific embodiment, the T lymphocyte survival motif is a CD28 T lymphocyte survival motif. In other specific embodiments, said T lymphocyte survival motif is an intracellular signaling domain of IL-7 receptor (IL-7R), an intracellular signaling domain of IL-12 receptor, an intracellular signaling domain of IL-15 receptor, an intracellular signaling domain of IL-21 receptor, or an intracellular signaling domain of transforming growth factor β (TGFβ) receptor. In another more specific embodiment, said primary signaling polypeptide or said co-stimulatory polypeptide comprise a portion of a CD28 molecule that comprises a T lymphocyte survival motif. In a more specific embodiment, said primary signaling polypeptide or said co-stimulatory polypeptide comprise a CD28 molecule that comprises a T lymphocyte survival motif. In certain specific embodiments, said first intracellular signaling domain comprises a polypeptide sequence comprising an immunoreceptor tyrosine-based activation motif (ITAM). In a more specific embodiment, said polypeptide sequence is a CD3ζ signaling domain.

In certain specific embodiments, said first antigen is an antigen on a tumor cell. In a more specific embodiment, said tumor cell is a cell in a solid tumor. In another more specific embodiment, said tumor cell is a blood cancer cell. In another specific embodiment, said antigen is a tumor-associated antigen or a tumor-specific antigen. In more specific embodiments, said tumor-associated antigen or tumor-specific antigen is Her2, prostate stem cell antigen (PSCA), alpha-fetoprotein (AFP), carcinoembryonic antigen (CEA), cancer antigen-125 (CA-125), CA19-9, calretinin, MUC-1, epithelial membrane protein (EMA), epithelial tumor antigen (ETA), tyrosinase, melanoma-associated antigen (MAGE), CD34, CD45, CD99, CD117, chromogranin, cytokeratin, desmin, glial fibrillary acidic protein (GFAP), gross cystic disease fluid protein (GCDFP-15), HMB-45 antigen, protein melan-A (melanoma antigen recognized by T lymphocytes; MART-1), myo-D1, muscle-specific actin (MSA), neurofilament, neuron-specific enolase (NSE), placental alkaline phosphatase, synaptophysin, thyroglobulin, thyroid transcription factor-1, the dimeric form of the pyruvate kinase isoenzyme type M2 (tumor M2-PK), an abnormal ras protein, or an abnormal p53 protein.

In another specific embodiment, said second antigen is a growth factor, cytokine, or interleukin. The second antigen is a growth factor, cytokine, or interleukin associated with angiogenesis or vasculogenesis. In more specific embodiments, said second antigen is vascular endothelial growth factor (VEGF), basic fibroblast growth factor (bFGF), platelet-derived growth factor (PDGF), hepatocyte growth factor (HGF), insulin-like growth factor (IGF), or interleukin-8 (IL-8).

In another specific embodiment, signal transduction activation provided by said second antigen is non-antigenic, but is associated with hypoxia. In more specific embodiments, said stimulus is induced by activation of hypoxia-inducible factor-1α (HIF-1α), HIF-1β, HIF-2α, HIF-2β, HIF-3α, or HIF-3β.

In another specific embodiment, said second antigen is an interleukin.

In another specific embodiment, said second antigen is a damage associated molecular pattern molecule (DAMP; also known as an alarmin). In more specific embodiments, said DAMP is a heat shock protein, chromatin-associated protein high mobility group box 1 (HMGB1), S100A8 (also known as MRP8, or calgranulin A), S100A9 (also known as MRP14, or calgranulin B), serum amyloid A (SAA), deoxyribonucleic acid, adenosine triphosphate, uric acid, or heparin sulfate.

In certain specific embodiments, said second antigen is an antigen on an antibody that binds to an antigen presented by a tumor cell.

In a specific embodiment of any of the embodiments herein, said co-stimulatory polypeptide comprises one or more co-stimulatory domains. In specific embodiments, said one or more co-stimulatory domains comprises one or more of a co-stimulatory CD27 polypeptide sequence, a co-stimulatory CD28 polypeptide sequence, a co-stimulatory OX40 (CD134) polypeptide sequence, a co-stimulatory 4-1BB (CD137) polypeptide sequence, or a co-stimulatory inducible T-cell co-stimulatory (ICOS) polypeptide sequence.

In a specific embodiment, said primary signaling polypeptide comprises an extracellular tumor antigen-binding domain and a CD3ζ signaling domain, and wherein said co-stimulatory polypeptide comprises an antigen-binding domain wherein said antigen is an angiogenic or vasculogenic factor, and one or more co-stimulatory molecule signaling domains. Said angiogenic factor can be, e.g., VEGF. Said one or more co-stimulatory molecule signaling motifs can comprise, e.g., co-stimulatory signaling domains from each of CD28, OX40, and 4-1BB. In a more specific embodiment, said primary signaling polypeptide comprises an extracellular tumor antigen-binding domain and a CD3ζ signaling domain, and wherein said co-stimulatory polypeptide comprises an antigen-binding domain wherein said antigen is VEGF, and co-stimulatory signaling domains from each of CD28, OX40, and 4-1BB.

In a more specific embodiment, said primary signaling polypeptide or said co-stimulatory polypeptide comprises a T lymphocyte survival motif. In more specific embodiments, said T lymphocyte survival motif is, or is derived from, an intracellular signaling domain of IL-7 receptor (IL-7R), an intracellular signaling domain of IL-12 receptor, an intracellular signaling domain of IL-15 receptor, an intracellular signaling domain of IL-21 receptor, or an intracellular signaling domain of transforming growth factor β (TGFβ) receptor. In a more specific embodiment of said T lymphocyte, therefore, said primary signaling polypeptide comprises an extracellular tumor antigen-binding domain and a CD3ζ signaling domain, and wherein said co-stimulatory polypeptide comprises an antigen-binding domain wherein said antigen is VEGF, an IL-7 receptor intracellular T lymphocyte survival motif, and co-stimulatory signaling domains from each of CD28, OX40, and 4-1BB.

In another specific embodiment of the T lymphocyte, said first antigen is a tumor-specific antigen or a tumor-associated antigen, and said first intracellular signaling domain comprises a CD3ζ signaling domain; and wherein said co-stimulatory polypeptide comprises an antigen-binding domain that binds said second antigen, and co-stimulatory signaling domains from each of CD28, OX40, and 4-1BB. In a more specific embodiment, said co-stimulatory polypeptide further comprises an intracellular T lymphocyte survival motif, e.g., a T lymphocyte survival motif that is, or is derived from, an intracellular signaling domain of IL-7 receptor (IL-7R), an intracellular signaling domain of IL-12 receptor, an intracellular signaling domain of IL-15 receptor, an intracellular signaling domain of IL-21 receptor, or an intracellular signaling domain of transforming growth factor β (TGFβ) receptor.

In a specific embodiment of any of the T lymphocytes provided herein, said second antigen is VEGF or IL-4.

In another aspect, provided herein is a T lymphocyte comprising a cell death polypeptide, a co-stimulatory polypeptide comprising a first extracellular antigen binding domain that binds a first antigen, and a first intracellular signaling domain; and a primary signaling polypeptide comprising a second extracellular antigen binding domain binding a second antigen, or a receptor that binds said second antigen; and a second intracellular signaling domain, wherein said primary signaling polypeptide does not comprise a co-stimulatory domain; wherein said modified lymphocyte becomes maximally cytotoxic only when said first signaling domain and said second signaling domain are both activated by said first antigen and said second antigen, respectively. In a specific embodiment, binding of said first antigen to said first antigen binding domain without binding of said second antigen to said second binding domain, or binding of said second antigen to said second antigen binding domain without binding of first second antigen to said first binding domain induces anergy of said T lymphocyte, or non-responsiveness of said T lymphocyte to said first antigen. In a specific embodiment, said first antigen-binding domain and said antigen-binding domain are independently an antigen-binding portion of a receptor or an antigen-binding portion of an antibody. In another specific embodiment, either or both of said first antigen binding domain or said second antigen binding domain are scFv antibody fragments. In specific embodiments, said co-stimulatory polypeptide and/or said primary signaling polypeptide additionally comprise a transmembrane domain. In a more specific embodiment, said co-stimulatory polypeptide or said primary signaling polypeptide comprises a T lymphocyte survival motif, e.g., any of the T lymphocyte survival motifs described herein. In another specific embodiment, said first antigen is an antigen on a tumor cell, e.g., a cell in a solid tumor or a blood cancer cell. In a specific embodiment, said first antigen is a tumor-associated antigen or a tumor-specific antigen, e.g., Her2, prostate stem cell antigen (PSCA), alpha-fetoprotein (AFP), carcinoembryonic antigen (CEA), cancer antigen-125 (CA-125), CA19-9, calretinin, MUC-1, epithelial membrane protein (EMA), epithelial tumor antigen (ETA), tyrosinase, melanoma-associated antigen (MAGE), CD34, CD45, CD99, CD117, chromogranin, cytokeratin, desmin, glial fibrillary acidic protein (GFAP), gross cystic disease fluid protein (GCDFP-15), HMB-45 antigen, protein melan-A (melanoma antigen recognized by T lymphocytes; MART-1), myo-D1, muscle-specific actin (MSA), neurofilament, neuron-specific enolase (NSE), placental alkaline phosphatase, synaptophysin, thyroglobulin, thyroid transcription factor-1, the dimeric form of the pyruvate kinase isoenzyme type M2 (tumor M2-PK), an abnormal ras protein, an abnormal p53 protein, CD19, CD22, CD27, CD30, CD70, GD2 (ganglioside G2), EGFRvIII (epidermal growth factor variant III), sperm protein 17 (Sp17), mesothelin, PAP (prostatic acid phosphatase), prostein, TARP (T cell receptor gamma alternate reading frame protein), Trp-p8, or STEAP1 (six-transmembrane epithelial antigen of the prostate 1). In another specific embodiment, said tumor-associated antigen or tumor-specific antigen is integrin αvβ3 (CD61), galactin, K-Ras (V-Ki-ras2 Kirsten rat sarcoma viral oncogene), or Ral-B.

In certain specific embodiments, said second intracellular signaling domain comprises a polypeptide sequence comprising an immunoreceptor tyrosine-based activation motif (ITAM), e.g., a CD3ζ signaling domain. In a specific embodiment, said second antigen is a growth factor, cytokine, or interleukin. In another specific embodiment, said second antigen is a growth factor, cytokine, or interleukin associated with angiogenesis or vasculogenesis, e.g., VEGF, bFGF, PDGF, HGF, IGF, or IL-8. In other more specific embodiments, signal transduction by said second chimeric receptor is induced by activation of a hypoxia-associated factor, e.g., HIF-1α, HIF-1β, HIF-2α, HIF-2β, HIF-3α, or HIF-3β. In other specific embodiments, said second antigen is an interleukin. In other specific embodiments, said second antigen is a DAMP, e.g., a heat shock protein, HMGB1, S100A8, S100A9, SAA, DNA, ATP, uric acid, or heparin sulfate. In other specific embodiments, said second antigen is an administered peptide, e.g., an antibody or a synthetic polypeptide. In other specific embodiments, said second antigen is an antigen on an antibody that binds to an antigen presented by a tumor cell. In certain specific embodiments, said co-stimulatory polypeptide comprises one or more co-stimulatory domains, e.g., one or more of a co-stimulatory CD27 polypeptide sequence, a co-stimulatory CD28 polypeptide sequence, a co-stimulatory OX40 (CD134) polypeptide sequence, a co-stimulatory 4-1BB (CD137) polypeptide sequence, or a co-stimulatory inducible T-cell co-stimulatory (ICOS) polypeptide sequence. In any of the above embodiments, in a specific embodiment, said co-stimulatory polypeptide or said primary signaling polypeptide comprises a T lymphocyte survival motif, e.g., said T lymphocyte survival motif is, or is derived from, an intracellular signaling domain of IL-7 receptor (IL-7R), an intracellular signaling domain of IL-12 receptor, an intracellular signaling domain of IL-15 receptor, an intracellular signaling domain of IL-21 receptor, or an intracellular signaling domain of transforming growth factor β (TGFβ) receptor.

4.4. Isolated Polypeptides

Any of the polypeptides, comprising a CTLA4 or PD-1 transmembrane domain, provided herein, may be modified by, e.g., acylation, amidation, glycosylation, methylation, phosphorylation, sulfation, sumoylation, ubiquitylation, or the like. The polypeptides may be labeled with a label capable of providing a detectable signal, e.g., with radioisotopes and fluorescent compounds. One or more side chains of the first or second polypeptides may be derivatized, e.g., derivatization of lysinyl and amino terminal residues with succinic or other carboxylic acid anhydrides, or derivatization with, e.g., imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate. Carboxyl side groups, aspartyl or glutamyl, may be selectively modified by reaction with carbodiimides (R—N=C=N—R) such as 1-cyclohexyl-3-(2-morpholinyl-(4-ethyl)carbodiimide or 1-ethyl-3-(4-azonia-4,4-dimethylpentyl)carbodiimide.

4.5. Isolated Nucleic Acids

The polypeptides provided herein (e.g., chimeric receptors) can be encoded by polynucleotide sequences according to well-known methods in the art. The polynucleotides may be contained within any polynucleotide vector suitable for the transformation of immune cells, e.g., T lymphocytes. For example, T lymphocytes may be transformed using synthetic vectors, lentiviral or retroviral vectors, autonomously replicating plasmids, a virus (e.g., a retrovirus, lentivirus, adenovirus, or herpes virus), or the like, containing polynucleotides encoding the first and second polypeptides (e.g., chimeric receptors). Lentiviral vectors suitable for transformation of T lymphocytes include, but are not limited to, e.g., the lentiviral vectors described in U.S. Pat. Nos. 5,994,136; 6,165,782; 6,428,953; 7,083,981; and 7,250,299, the disclosures of which are hereby incorporated by reference in their entireties. HIV vectors suitable for transformation of T lymphocytes include, but are not limited to, e.g., the vectors described in U.S. Pat. No. 5,665,577, the disclosure of which is hereby incorporated by reference in its entirety.

Nucleic acids useful in the production of the first and second polypeptides, e.g., within a T lymphocyte, include DNA, RNA, or nucleic acid analogs. Nucleic acid analogs can be modified at the base moiety, sugar moiety, or phosphate backbone, and can include deoxyuridine substitution for deoxythymidine, 5-methyl-2'-deoxycytidine or 5-bromo-2'-deoxycytidine substitution for deoxycytidine. Modifications of the sugar moiety can include modification of the 2' hydroxyl of the ribose sugar to form 2'-O-methyl or 2'-O- allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, for example, Summerton and Weller (1997) Antisense Nucleic Acid Drug Dev. 7:187-195; and Hyrup et al. (1996) Bioorgan. Med. Chain. 4:5-23. In addition, the deoxyphosphate backbone can be replaced with, for example, a phosphorothioate or phosphorodithioate backbone, a phosphoroamidite, or an alkyl phosphotriester backbone.

4.6. Cells

Non-limiting examples of cells in which the cell death polypeptides and multimerizing or dimerizing agents may be used include, but are not limited to, natural killer (NK) cells, dendritic cells (DC), placental stem cells (e.g., the placental stem cells disclosed in U.S. Pat. Nos. 7,468,276; 8,057,788 and 8,202,703, the disclosures of which are hereby incorporated by reference in their entireties), mesenchymal-like stem cells from umbilical cord blood, placental blood, peripheral blood, bone marrow, dental pulp, adipose tissue, osteochondral tissue, and the like; embryonic stem cells, embryonic germ cells, neural crest stem cells, neural stem cells, and differentiated cells (e.g., fibroblasts, etc.). The cell death polypeptides, and multimerizing or dimerizing agents, may also be used in tumor cell lines, e.g., for animal model experimental purposes.

In a specific embodiment, the cells comprising the polypeptides provided herein are T lymphocytes. The T lymphocytes comprising the polypeptides provided herein may be naive T lymphocytes or MHC-restricted T lymphocytes. In certain embodiments, the T lymphocytes are tumor infiltrating lymphocytes (TILs). In certain embodiments, the T lymphocytes have been isolated from a tumor biopsy, or have been expanded from T lymphocytes isolated from a tumor biopsy. In certain other embodiments, the T lymphocytes have been isolated from, or are expanded from T lymphocytes expanded from, peripheral blood, cord blood, or lymph.

The immune cells, e.g., T lymphocytes, used in the present methods are preferably autologous to an individual to whom the T lymphocytes are to be administered. In certain other embodiments, the T lymphocytes are allogeneic to an individual to whom the T lymphocytes are to be administered. Where allogeneic T lymphocytes are used to prepare T lymphocytes, it is preferable to select T lymphocytes that will reduce the possibility of graft-versus-host disease (GVHD) in the individual. For example, in certain embodiments, virus-specific T lymphocytes are selected for preparation of T lymphocytes; such lymphocytes will be expected to have a greatly reduced native capacity to bind to, and thus become activated by, any recipient antigens. In certain embodiments, recipient-mediated rejection of allogeneic T lymphocytes can be reduced by co-administration to the host of one or more immunosuppressive agents, e.g., cyclosporine, tacrolimus, sirolimus, cyclophosphamide, or the like.

In one embodiment, T lymphocytes are obtained from an individual, optionally then expanded, and then transformed with a polynucleotide encoding a cell death polypeptide, and optionally one or more polynucleotides encoding one or more CAR(s), and optionally then expanded. In another embodiment, T lymphocytes are obtained from an individual, optionally then expanded, and then transformed with a polynucleotide encoding a cell death polypeptide, and optionally one or more polynucleotides encoding one or more CAR(s), and optionally then expanding. Cells containing any of the polynucleotide may be selected using one or more selectable markers.

In certain embodiments, any of the T lymphocytes provided herein express or comprise native TCR proteins, e.g., TCR-α and TCR-β that are capable of forming native TCR complexes, in addition to the CTLA4 or PD-1 transmembrane domain-containing polypeptide. In certain other embodiments, either or both of the native genes encoding TCR-α and TCR-β in the T lymphocytes are modified to be non-functional, e.g., a portion or all are deleted, a mutation is inserted, etc.

In certain embodiments, any of the T lymphocytes provided herein are isolated from a tumor lesion, e.g., are tumor-infiltrating lymphocytes; such T lymphocytes are expected to be specific for a TSA or TAA.

T lymphocytes, and T lymphocytes comprising a polypeptide comprising a CD3ζ signaling domain and a CD28 co-stimulatory domain can be expanded using antibodies to CD3 and CD28, e.g., antibodies attached to beads, or to the surface of a cell culture plate; see, e.g., U.S. Pat. Nos. 5,948,893; 6,534,055; 6,352,694; 6,692,964; 6,887,466; and 6,905,681.

In any of the above embodiments, the antigen and/or antibody can exist free in the medium in which the T lymphocytes are cultures, or either or both can be attached to a solid support, e.g., tissue culture plastic surface, beads, or the like.

The T lymphocytes provided herein can optionally comprise a second type of "suicide gene" or "safety switch", in addition to the cell death polypeptide. For example, the T lymphocytes, in certain embodiments, can comprise an HSV thymidine kinase gene (HSV-TK), which causes death of the T lymphocytes upon contact with gancyclovir. In another embodiment, the T lymphocytes express or comprise an inducible caspase, e.g., an inducible caspase 9 (icaspase9), e.g., a fusion protein between caspase 9 and human FK506 binding protein allowing for dimerization using a specific small molecule pharmaceutical. See Straathof et al., *Blood* 105(11):4247-4254 (2005).

4.7. Methods of Using Cells Comprising Cell Death Polypeptides

The cells, e.g., T lymphocytes, provided herein that comprise cell death polypeptides and optionally one or more CARs, as described elsewhere herein, can be used to treat an individual having one or more types of cells desired to be targeted by the cells described herein, e.g., one or more types of cells to be killed. In certain embodiments, the cells to be killed are cancer cells, e.g., tumor cells. In specific embodiments, the cancer cells are cells of a solid tumor. In specific embodiments, the cells are cells of a lymphoma, a lung cancer, a breast cancer, a prostate cancer, an adrenocortical carcinoma, a thyroid carcinoma, a nasopharyngeal carcinoma, a melanoma, e.g., a malignant melanoma, a skin carcinoma, a colorectal carcinoma, a desmoid tumor, a desmoplastic small round cell tumor, an endocrine tumor, an Ewing sarcoma, a peripheral primitive neuroectodermal tumor, a solid germ cell tumor, a hepatoblastoma, a neuroblastoma, a non-rhabdomyosarcoma soft tissue sarcoma, an osteosarcoma, a retinoblastoma, a rhabdomyosarcoma, a Wilms tumor, a glioblastoma, a myxoma, a fibroma, a lipoma, or the like. In more specific embodiments, said lymphoma can be chronic lymphocytic leukemia (small lymphocytic lymphoma), B-cell prolymphocytic leukemia, lymphoplasmacytic lymphoma, Waldenström macroglobulinemia, splenic marginal zone lymphoma, plasma cell myeloma, plasmacytoma, extranodal marginal zone B cell lymphoma, MALT lymphoma, nodal marginal zone B cell lymphoma, follicular lymphoma, mantle cell lymphoma, diffuse large B cell lymphoma, mediastinal (thymic) large B cell lymphoma, intravascular large B cell lymphoma, primary effusion lymphoma, Burkitt's lymphoma, T lymphocyte prolymphocytic leukemia, T lymphocyte large granular lymphocytic leukemia, aggressive NK cell leukemia, adult T lymphocyte leukemia/lymphoma, extranodal NK/T lymphocyte lymphoma, nasal type, enteropathy-type T lymphocyte lymphoma, hepatosplenic T lymphocyte lymphoma, blastic NK cell lymphoma, mycosis fungoides, Sezary syndrome, primary cutaneous anaplastic large cell lymphoma, lymphomatoid papulosis, angioimmunoblastic T lymphocyte lymphoma, peripheral T lymphocyte lymphoma (unspecified), anaplastic large cell lymphoma, Hodgkin lymphoma, or a non-Hodgkin lymphoma.

In certain embodiments, when the modified cells, e.g., modified T lymphocytes described herein are administered to a subject in need thereof, the combination of multimerizing agent and cell death polypeptide selected are chosen such that they are compatible with the patient population (or subpopulation) in which the cells, e.g., T lymphocytes, have been administered. By way of example only, if the multimerizing agent selected is the antibody rituximab, then in certain embodiments the patient population is individuals having a cancer of the B cells, e.g., B cell lymphoma.

Efficacy of the cells, e.g., T lymphocytes, after administration to an individual having a disease or disorder remediable by such cells, e.g., T lymphocytes, e.g., an individual having cancer, can be assessed by one or more criteria, specific to the particular disease or disorder, known to those of ordinary skill in the art, to be indicative of progress of the disease or disorder. Generally, administration of the cells to such an individual is effective when one or more of said criteria detectably, e.g., significantly, moves from a disease state value or range to, or towards, a normal value or range.

The cells, e.g., T lymphocytes, may be formulated in any pharmaceutically-acceptable solution, preferably a solution suitable for the delivery of living cells, e.g., saline solution (such as Ringer's solution), gelatins, carbohydrates (e.g., lactose, amylose, starch, or the like), fatty acid esters, hydroxymethylcellulose, polyvinyl pyrolidine, etc. Such preparations are preferably sterilized prior to addition of the cells, and may be mixed with auxiliary agents such as lubricants, preservatives, stabilizers, emulsifiers, salts for influencing osmotic pressure, buffers, and coloring. Pharmaceutical carriers suitable for use in formulating the cells are known in the art and are described, for example, in WO 96/05309.

In certain embodiments, the cells, e.g., T lymphocytes, are formulated into individual doses, wherein said individual doses comprise at least, at most, or about $1\times10^4$, $5\times10^4$, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, or $1\times10^{11}$ T lymphocytes. In certain embodiments, the cells are formulated for intravenous, intraarterial, parenteral, intramuscular, subcutaneous, intrathecal, or intraocular administration, or administration within a particular organ or tissue.

5. EXAMPLES

5.1. Example 1

Treatment of B Cell Lymphoma

An individual presents with B-cell chronic lymphocytic leukemia, a B cell lymphoma. Testing of B cells from the individual determines that the B cells carry a 17p deletion. T lymphocytes are obtained from the individual, transfected with a lentiviral vector comprising a nucleotide sequence that encodes a chimeric antigen receptor (CAR), and transfected with a second lentiviral vector comprising a nucleotide sequence encoding a dimerizable cell death polypeptide comprising an extracellular domain that comprises a mimotope that can be bound by the antibody rituximab, and an intracellular domain that comprises a caspase 9 domain. The T lymphocytes are expanded using CD3+CD28-coated beads to sufficient numbers for administration. The chimeric receptor comprises an extracellular antigen-binding region that binds to CD19; a transmembrane domain from CTLA4; intracellular co-stimulatory domain from CD28; and an intracellular CD3ζ domain. The individual is administered between $10^9$ and $10^{10}$ of the T lymphocytes in 200 mL saline solution by intravenous infusion over 30 minutes. The individual is monitored for two weeks afterwards to establish a reduction of at least 90% of CD19+ B cells in the individual's blood. Where the patient, after administration of the T lymphocytes, shows signs of distress due to the T lymphocytes (e.g., difficulty breathing, fever, abnormal serum cytokine levels, rash, or the like), rituximab is administered at a dosage of 200-500 mg/m$^2$ or until symptoms abate.

5.2. Example 2

Treatment of a B Cell Lymphoma

An individual presents with B-cell chronic lymphocytic leukemia, a B cell lymphoma. Testing of B cells from the individual determines that the B cells carry a 17p deletion. About $10^6$ T lymphocytes are obtained from the individual, transfected with a lentiviral vector comprising a nucleotide sequence encoding a cell death polypeptide comprising an extracellular domain that comprises a mimotope that can be bound by the antibody rituximab and an intracellular domain that comprises a caspase 8 domain, and transfected with a lentiviral vector comprising a nucleotide sequence that encodes a CAR. The CAR comprises an extracellular antigen-binding region that binds to CD19; a transmembrane domain from PD-1; intracellular co-stimulatory domain from CD28; and an intracellular CD3ζ domain. CAR-expressing T lymphocytes are administered to the individual without prior expansion of the T lymphocytes. The individual is administered between $10^5$ and $10^6$ of the T lymphocytes in 200 mL saline solution by intravenous infusion over 30 minutes. The individual is monitored for two weeks afterwards to establish a reduction of at least 90% of CD19+ B cells in the individual's blood. Where the patient, after administration of the T lymphocytes, shows signs of distress due to the T lymphocytes (e.g., difficulty breathing, fever, abnormal serum cytokine levels, rash, or the like), rituximab is administered at a dosage of 200-500 mg/m$^2$ or until symptoms abate.

5.3. Example 3

Treatment of B Cell Lymphoma

An individual presents with B-cell chronic lymphocytic leukemia, a B cell lymphoma. Testing of B cells from the individual determines that the B cells carry a p53 deletion. T lymphocytes are obtained from the individual, transfected with a lentiviral vector comprising a nucleotide sequence encoding a cell death polypeptide comprising an extracellular domain that comprises an epitope that can be bound by the antibody rituximab and an intracellular domain that comprises a caspase 3 domain, and transfected with a lentiviral vector comprising a nucleotide sequence that encodes a CAR. The T lymphocytes are expanded using CD3+CD28-coated beads to sufficient numbers for administration. The CAR comprises an extracellular antigen-binding region that binds to CD19; a transmembrane domain from CTLA4; intracellular co-stimulatory domains from each of CD28, 4-1BB, and OX40; and an intracellular CD3ζ domain. The individual is administered between $10^9$ and $10^{10}$ of the T lymphocytes in 200 mL saline solution by intravenous infusion over 30 minutes. The individual is monitored for two weeks afterwards to establish a reduction of at least 90% of CD19+ B cells in the individual's blood. Where the patient, after administration of the T lymphocytes, shows signs of distress due to the T lymphocytes (e.g., difficulty breathing, fever, abnormal serum cytokine levels, rash, or the like), rituximab is administered at a dosage of 200-500 mg/m$^2$ or until symptoms abate.

5.4. Example 4

Treatment of a B Cell Lymphoma

An individual presents with B-cell chronic lymphocytic leukemia, a B cell lymphoma. Testing of B cells from the individual determines that the B cells carry a p53 deletion. About $10^6$ T lymphocytes are obtained from the individual, transfected with a lentiviral vector comprising a nucleotide sequence encoding a cell death polypeptide comprising an extracellular domain that comprises an epitope that can be bound by the antibody rituximab and an intracellular domain that comprises a caspase 9 domain, and transfected with a lentiviral vector comprising a nucleotide sequence that encodes a CAR. The CAR comprises an extracellular antigen-binding region that binds to CD19; a transmembrane domain from PD-1; intracellular co-stimulatory domains from each of CD28, 4-1BB, and OX40; and an intracellular CD3ζ domain. CAR-expressing T lymphocytes are administered to the individual without prior expansion of the T lymphocytes. The individual is administered between $10^5$ and $10^6$ of the T lymphocytes in 200 mL saline solution by intravenous infusion over 30 minutes. The individual is monitored for two weeks afterwards to establish a reduction of at least 90% of CD19+ B cells in the individual's blood. Where the patient, after administration of the T lymphocytes, shows signs of distress due to the T lymphocytes (e.g., difficulty breathing, fever, abnormal serum cytokine levels, rash, or the like), rituximab is administered at a dosage of 200-500 mg/m$^2$ or until symptoms abate.

5.5. Example 5

Treatment of Prostate Cancer

An individual presents with stage T2 prostate cancer, with no spread to regional or other lymph nodes (N0, M0). Histological grade is determined to be G2. Overall, the individual is determined to have Stage II prostate cancer. The individual is administered between $10^9$ and $10^{10}$ T lymphocytes that comprise a CAR, in 200 mL saline solution by intravenous infusion over 30 minutes. The CAR comprises an extracellular antigen-binding region that binds to PSCA, a transmembrane domain from CTLA4, intracellular co-stimulatory domain from CD28, and an intracellular CD3ζ domain. The T lymphocytes also comprise a cell death polypeptide comprising an extracellular domain that comprises an epitope that can be bound by the antibody rituximab, and an intracellular domain that comprises a caspase 3, caspase 8, or caspase 9 domain. The individual is re-assessed for prostate cancer stage and spread to lymph nodes, and histology of biopsied prostate tissue is performed, at 30, 60 and 90 days post-administration. Where the patient, after administration of the T lymphocytes, shows signs of distress due to the T lymphocytes (e.g., difficulty breathing, fever, abnormal serum cytokine levels, rash, or the like), rituximab is administered at a dosage of 200-500 mg/m$^2$ or until symptoms abate.

5.6. Example 6

Treatment of Prostate Cancer

An individual presents with stage T2 prostate cancer, with no spread to regional or other lymph nodes (N0, M0). Histological grade is determined to be G2. Overall, the individual is determined to have Stage II prostate cancer. The individual is administered between $10^9$ and $10^{10}$ T lymphocytes that comprise a CAR, in 200 mL saline solution by intravenous infusion over 30 minutes. The CAR comprises an extracellular antigen-binding region that binds to PSCA, a transmembrane domain from PD-1, intracellular co-stimulatory domain from CD28, and an intracellular CD3ζ domain. The T lymphocytes also comprise a cell death polypeptide comprising an extracellular domain that comprises an epitope that can be bound by the antibody rituximab, and an intracellular domain that comprises a caspase 3, caspase 8, or caspase 9 domain. The individual is re-assessed for prostate cancer stage and spread to lymph nodes, and histology of biopsied prostate tissue is performed, at 30, 60 and 90 days post-administration. Where the patient, after administration of the T lymphocytes, shows signs of distress due to the T lymphocytes (e.g., difficulty breathing, fever, abnormal serum cytokine levels, rash, or the like), rituximab is administered at a dosage of 200-500 mg/m$^2$ or until symptoms abate.

5.7. Example 7

Treatment of Prostate Cancer

An individual presents with stage T2 prostate cancer, with no spread to regional or other lymph nodes (N0, M0). Histological grade is determined to be G2. Overall, the individual is determined to have Stage II prostate cancer. The individual is administered between $10^9$ and $10^{10}$ T lymphocytes that comprise a CAR, in 200 mL saline solution by intravenous infusion over 30 minutes. The CAR comprises an extracellular antigen-binding region that binds to PSCA, a transmembrane domain from CTLA-4, intracellular co-stimulatory domains from each of CD28, 4-1BB, and OX40, and an intracellular CD3ζ domain. The T lymphocytes also comprise a cell death polypeptide comprising an extracellular domain that comprises an epitope that can be bound by the antibody rituximab, and an intracellular domain that comprises a caspase 3, caspase 8, or caspase 9 domain. The individual is re-assessed for prostate cancer stage and spread to lymph nodes, and histology of biopsied prostate tissue is performed, at 30, 60 and 90 days post-administration. Where the patient, after administration of the T lymphocytes, shows signs of distress due to the T lymphocytes (e.g., difficulty breathing, fever, abnormal serum cytokine levels, rash, or the like), rituximab is administered at a dosage of 200-500 mg/m² or until symptoms abate.

5.8. Example 8

Treatment of Prostate Cancer

An individual presents with stage T2 prostate cancer, with no spread to regional or other lymph nodes (N0, M0). Histological grade is determined to be G2. Overall, the individual is determined to have Stage II prostate cancer. The individual is administered between $10^9$ and $10^{10}$ T lymphocytes that comprise a CAR, in 200 mL saline solution by intravenous infusion over 30 minutes. The CAR comprises an extracellular antigen-binding region that binds to PSCA, a transmembrane domain from PD-1, intracellular co-stimulatory domains from each of CD28, 4-1BB, and OX40, and an intracellular CD3ζ domain. The T lymphocytes also comprise a cell death polypeptide comprising an extracellular domain that comprises an epitope that can be bound by the antibody rituximab, and an intracellular domain that comprises a caspase 3, caspase 8, or caspase 9 domain. The individual is re-assessed for prostate cancer stage and spread to lymph nodes, and histology of biopsied prostate tissue is performed, at 30, 60 and 90 days post-administration. Where the patient, after administration of the T lymphocytes, shows signs of distress due to the T lymphocytes (e.g., difficulty breathing, fever, abnormal serum cytokine levels, rash, or the like), rituximab is administered at a dosage of 200-500 mg/m² or until symptoms abate.

EQUIVALENTS

The present disclosure is not to be limited in scope by the specific embodiments described herein. Indeed, various modifications of the subject matter provided herein, in addition to those described, will become apparent to those skilled in the art from the foregoing description. Such modifications are intended to fall within the scope of the appended claims.

Various publications, patents and patent applications are cited herein, the disclosures of which are incorporated by reference in their entireties.

What is claimed is:

1. A T lymphocyte comprising an artificial cell death polypeptide comprising an apoptosis-inducing domain, wherein said artificial cell death polypeptide is a transmembrane protein comprising an extracellular domain that comprises a CD20 epitope, a transmembrane domain, and an intracellular domain comprising said apoptosis-inducing domain, wherein said apoptosis-inducing domain is caspase 3, caspase 8 or caspase 9, wherein said polypeptide is dimerizable using an anti-CD20 antibody that binds to said CD20 epitope, and wherein when said antibody dimerizes said polypeptide, an apoptosis-inducing signal is generated in said T lymphocyte.

2. The T lymphocyte of claim 1, wherein said antibody has been approved by the United States Food and Drug Administration for any use.

3. The T lymphocyte of claim 1, wherein said antibody is rituximab and said extracellular domain comprises a CD20 epitope to which said rituximab binds.

4. The T lymphocyte of claim 1 that additionally comprises a chimeric antigen receptor (CAR) that recognizes an antigen on a tumor cell.

5. The T lymphocyte of claim 4, wherein said tumor cell is a cell in a solid tumor.

6. The T lymphocyte of claim 4, wherein said tumor cell is a cell of a blood cancer.

7. The T lymphocyte of claim 4, wherein said antigen is Her2, prostate stem cell antigen, alpha-fetoprotein, carcinoembryonic antigen, cancer antigen-125, CA19-9, calretinin, MUC-1, epithelial membrane protein, epithelial tumor antigen, tyrosinase, melanoma-associated antigen, CD34, CD45, CD99, CD117, chromogranin, cytokeratin, desmin, glial fibrillary acidic protein, gross cystic disease fluid protein, HMB-45 antigen, protein melan-A, myo-D1, muscle-specific actin, neurofilament, neuron-specific enolase, placental alkaline phosphatase, synaptophysis, thyroglobulin, thyroid transcription factor-1, or the dimeric form of the pyruvate kinase isoenzyme type M2.

8. A method of killing a T lymphocyte, wherein said T lymphocyte comprises a plurality of artificial cell death polypeptides each comprising an apoptosis-inducing domain, wherein said artificial cell death polypeptide is a transmembrane protein comprising an extracellular domain that comprises a CD20 epitope, a transmembrane domain, and an intracellular domain comprising said apoptosis-inducing domain, wherein said apoptosis-inducing domain is caspase 3, caspase 8 or caspase 9, wherein said polypeptide is dimerizable using an anti-CD20 antibody that binds to said CD20 epitope, and wherein when said antibody dimerizes said polypeptides, an apoptosis-inducing signal is generated in said T lymphocyte,
   comprising contacting said T lymphocyte with an amount of said antibody sufficient for said plurality of artificial cell death polypeptides to dimerize and generate an aggregate apoptosis-inducing signal sufficient to kill said T lymphocyte.

9. The method of claim 8, wherein said antibody has been approved by the United States Food and Drug Administration for any use.

10. The method of claim 8, wherein said antibody is rituximab and said extracellular domain comprises a CD20 epitope that binds to said rituximab.

11. The method of claim 8 wherein said T lymphocyte additionally comprises a chimeric antigen receptor (CAR) that recognizes an antigen on a tumor cell.

12. The method of claim 11, wherein said antigen is Her2, prostate stem cell antigen, alpha-fetoprotein, carcinoembryonic antigen, cancer antigen-125, CA19-9, calretinin, MUC-1, epithelial membrane protein, epithelial tumor antigen, tyrosinase, melanoma-associated antigen, CD34, CD45, CD99, CD117, chromogranin, cytokeratin, desmin, glial fibrillary acidic protein, gross cystic disease fluid protein, HMB-45 antigen, protein melan-A, myo-D1, muscle-specific actin, neurofilament, neuron-specific enolase, placental alkaline phosphatase, synaptophysis, thyroglobulin, thyroid transcription factor-1, or the dimeric form of the pyruvate kinase isoenzyme type M2.

* * * * *

SEQUENCE LISTING

```
<160> NUMBER OF SEQ ID NOS: 8

<210> SEQ ID NO 1
<211> LENGTH: 36
<212> TYPE: PRT
<213> ORGANISM: Homo sapiens
<220> FEATURE:
<223> OTHER INFORMATION: sequence of CTLA4 transmembrane domain

<400> SEQUENCE: 1

Pro Glu Pro Cys Pro Asp Ser Asp Phe Leu Leu Trp Ile Leu Ala Ala
1               5                   10                  15

Val Ser Ser Gly Leu Phe Phe Tyr Ser Phe Leu Leu Thr Ala Val Ser
            20                  25                  30

Leu Ser Lys Met
        35

<210> SEQ ID NO 2
<211> LENGTH: 29
<212> TYPE: PRT
<213> ORGANISM: Homo sapiens
<220> FEATURE:
<223> OTHER INFORMATION: sequence of CTLA4 transmembrane domain

<400> SEQUENCE: 2

Pro Asp Ser Asp Phe Leu Leu Trp Ile Leu Ala Ala Val Ser Ser Gly
1               5                   10                  15

Leu Phe Phe Tyr Ser Phe Leu Leu Thr Ala Val Ser Leu
            20                  25

<210> SEQ ID NO 3
<211> LENGTH: 23
<212> TYPE: PRT
<213> ORGANISM: Homo sapiens
<220> FEATURE:
<223> OTHER INFORMATION: sequence of CTLA4 transmembrane domain

<400> SEQUENCE: 3

Phe Leu Leu Trp Ile Leu Ala Ala Val Ser Ser Gly Leu Phe Phe Tyr
1               5                   10                  15

Ser Phe Leu Leu Thr Ala Val
```

-continued

```
<210> SEQ ID NO 4
<211> LENGTH: 21
<212> TYPE: PRT
<213> ORGANISM: Homo sapiens
<220> FEATURE:
<223> OTHER INFORMATION: sequence of CTLA4 transmembrane domain

<400> SEQUENCE: 4

Phe Leu Leu Trp Ile Leu Ala Ala Val Ser Ser Gly Leu Phe Phe Tyr
1               5                   10                  15

Ser Phe Leu Leu Thr
            20

<210> SEQ ID NO 5
<211> LENGTH: 26
<212> TYPE: PRT
<213> ORGANISM: Artificial Sequence
<220> FEATURE:
<223> OTHER INFORMATION: sequence of CTLA4 transmembrane domain

<400> SEQUENCE: 5

Phe Leu Leu Trp Ile Leu Val Ala Val Ser Leu Gly Leu Phe Phe Tyr
1               5                   10                  15

Ser Phe Leu Val Ser Ala Val Ser Leu Ser
            20                  25

<210> SEQ ID NO 6
<211> LENGTH: 29
<212> TYPE: PRT
<213> ORGANISM: Artificial Sequence
<220> FEATURE:
<223> OTHER INFORMATION: sequence of PD-1 transmembrane domain

<400> SEQUENCE: 6

Thr Leu Val Val Gly Val Val Gly Gly Leu Leu Gly Ser Leu Val Leu
1               5                   10                  15

Leu Val Trp Val Leu Ala Val Ile Cys Ser Arg Ala Ala
            20                  25

<210> SEQ ID NO 7
<211> LENGTH: 21
<212> TYPE: PRT
<213> ORGANISM: Homo sapiens
<220> FEATURE:
<223> OTHER INFORMATION: sequence of PD-1 transmembrane domain

<400> SEQUENCE: 7

Val Gly Val Val Gly Gly Leu Leu Gly Ser Leu Val Leu Leu Val Trp
1               5                   10                  15

Val Leu Ala Val Ile
            20

<210> SEQ ID NO 8
<211> LENGTH: 26
<212> TYPE: PRT
<213> ORGANISM: Unknown
<220> FEATURE:
<223> OTHER INFORMATION: sequence of PD-1 transmembrane domain
```

```
<400> SEQUENCE: 8

Phe Gln Thr Leu Val Val Gly Val Val Gly Gly Leu Leu Gly Ser Leu
1               5                  10                 15

Val Leu Leu Val Trp Val Leu Ala Val Ile
            20                  25
```